United States Patent
Sugiura et al.

(10) Patent No.: US 9,908,972 B2
(45) Date of Patent: Mar. 6, 2018

(54) PHOTODEGRADABLE CROSS-LINKING AGENT, PHOTODEGRADABLE GEL, CELL CULTURE INSTRUMENT, CELL ARRANGEMENT-SORTING APPARATUS, CELL ARRANGEMENT METHOD, CELL SORTING METHOD, TISSUE FORMING METHOD, AND TISSUE

(71) Applicant: National Institute of Advanced Industrial Science and Technology, Tokyo (JP)

(72) Inventors: Shinji Sugiura, Tsukuba (JP); Toshiyuki Takagi, Ushiku (JP); Fumiki Yanagawa, Tsukuba (JP); Kimio Sumaru, Tsukuba (JP); Toshiyuki Kanamori, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 169 days.

(21) Appl. No.: 14/892,267

(22) PCT Filed: May 13, 2014

(86) PCT No.: PCT/JP2014/062725
§ 371 (c)(1),
(2) Date: Nov. 19, 2015

(87) PCT Pub. No.: WO2014/188911
PCT Pub. Date: Nov. 27, 2014

(65) Prior Publication Data
US 2016/0177030 A1    Jun. 23, 2016

(30) Foreign Application Priority Data
May 22, 2013  (JP) ................................ 2013-108429

(51) Int. Cl.
| | | |
|---|---|---|
| C08G 65/333 | (2006.01) | |
| C08G 69/40 | (2006.01) | |
| C08G 81/00 | (2006.01) | |
| C12N 5/00 | (2006.01) | |
| C12M 1/00 | (2006.01) | |

(52) U.S. Cl.
CPC ..... *C08G 65/33389* (2013.01); *C08G 65/333* (2013.01); *C08G 65/33337* (2013.01); *C08G 69/40* (2013.01); *C08G 81/00* (2013.01); *C12M 23/20* (2013.01); *C12M 23/30* (2013.01); *C12N 5/0068* (2013.01); *C12N 2537/10* (2013.01)

(58) Field of Classification Search
CPC .............................................. C08G 65/33389
See application file for complete search history.

(56) References Cited

U.S. PATENT DOCUMENTS

| | | | | |
|---|---|---|---|---|
| 4,203,975 | A | * 5/1980 | Greven .................... | C07K 7/16 514/17.5 |
| 5,624,839 | A | * 4/1997 | Yada .................. | C08B 37/0063 435/378 |
| 5,980,861 | A | * 11/1999 | Hnatowich .......... | A61K 51/088 424/1.11 |
| 2003/0220245 | A1* | 11/2003 | Hubbell ............... | A61K 31/337 525/50 |
| 2007/0093639 | A1* | 4/2007 | Jassen ................. | C08G 18/714 528/327 |
| 2007/0190036 | A1* | 8/2007 | Kizilel .................... | A61K 9/06 424/93.7 |
| 2009/0036403 | A1 | 2/2009 | Stroumpoulis et al. | |

FOREIGN PATENT DOCUMENTS

| | | |
|---|---|---|
| JP | 2007-108087 | 4/2007 |
| JP | 2009-542843 | 12/2009 |
| JP | 2010-059322 | 3/2010 |
| JP | 2010-508428 | 3/2010 |
| JP | 2012-080844 | 4/2012 |
| JP | 2012-125218 | 7/2012 |
| JP | 2014-226088 | 12/2014 |
| WO | WO 00/33764 A1 | 6/2000 |
| WO | WO 2008/005207 A2 | 1/2008 |
| WO | WO 2008/055666 A1 | 5/2008 |

OTHER PUBLICATIONS

Murayama et al. Anal. Chem. 2010, 82, 2186-2191 (Year: 2010).*
International Search Report dated Aug. 19, 2014 in corresponding PCT International Application No. PCT/JP2014/062725.
Written Opinion dated Aug. 19, 2014 in corresponding PCT International Application No. PCT/JP2014/062725.
J.W. Scannell et al., "Diagnosing the decline in pharmaceutical R&D efficiency," Nat. Rev. Drug Discov. (2012) vol. 11, pp. 191-200.
F. Pammolli et al., "The productivity crisis in pharmaceutical R&D," Nat. Rev. Drug Discov. (2011) vol. 10, pp. 428-438.
J.L. Drury et al., "Hydrogels for tissue engineering: scaffold design variables and applications," Biomaterials (2003) vol. 24, pp. 4337-4351.
A.M. Kloxin et al "Photodegradable Hydrogels for Dynamic Tuning of Physical and Chemical Properties," Science (2009) vol. 324, pp. 59-63.

(Continued)

*Primary Examiner* — Matthew P Coughlin
(74) *Attorney, Agent, or Firm* — Ostrolenk Faber LLP

(57) ABSTRACT

The present invention provides a photodegradable cross-linking agent capable of manufacturing a photodegradable gel, which has appropriate moisture content and water solubility as a cell carrier and has strength that makes it possible to construct a complicated three-dimensional microstructure. The photodegradable cross-linking agent of the present invention includes a main chain 2 which is composed of branched polyethylene glycol having three or more branched chains and a photodegradable benzyl group 3 which is disposed on the terminus of the branched chains, in which the benzyl group has an active ester group 4, which is reactive with an amino group or a hydroxyl group, and one or more nitro groups in a benzene ring.

5 Claims, 25 Drawing Sheets

(56) References Cited

OTHER PUBLICATIONS

A.M. Kloxin et al., "Tunable Hydrogels for External Manipulation of Cellular Microenvironments through Controlled Photodegradation," Adv. Mater. (2010) vol. 22, pp. 61-66.

D.Y. Wong et al., "Photodegradable Hydrogels to Generate Positive and Negative Features over Multiple Length Scales," Macromolecules (2010) vol. 43, pp. 2824-2831.

A.M. Kloxin et al., "In Situ elasticity modulation with dynamic substrates to direct cell phenotype," Biomaterial. (2010) vol. 31, pp. 1-8.

K. Kikuchi et al. "Stepwise Assembly of Micropatterned Co-cultures Using Photoresponsvie Culture Surfaces and Its Application to Hepatic Tissue Array," Biotechnol. Bioeng. (2009) vol. 103, pp. 552-561.

J.W. Nichol et al. "Cell-laden microengineered gelatin methacrylate hydrogels," Biomaterials (2010) vol. 31, pp. 5536-5544.

Xueguang Jiang et al. "Multiple Micellization and Dissociation Transitions of Thermo-and Light-Sensitive Poly(ethylene oxide)-b-poly(ethoxytri(ethylene glycol)acrylate-co-o-nitrobenzyl acrylate) in Water," Macromolecules (2008) vol. 41, Issue 7, pp. 2632-2643.

Shinji Sugiura, et al., "A Photodegradable Hydrogel Sheet for Microscale Optical Control of Cell Adhesion and Detachment," 16$^{th}$ International Conference on Miniaturized Systems for Chemistry and Life Sciences, Oct. 28-Nov. 1, 2012, Okinawa, Japan, pp. 671-673.

* cited by examiner

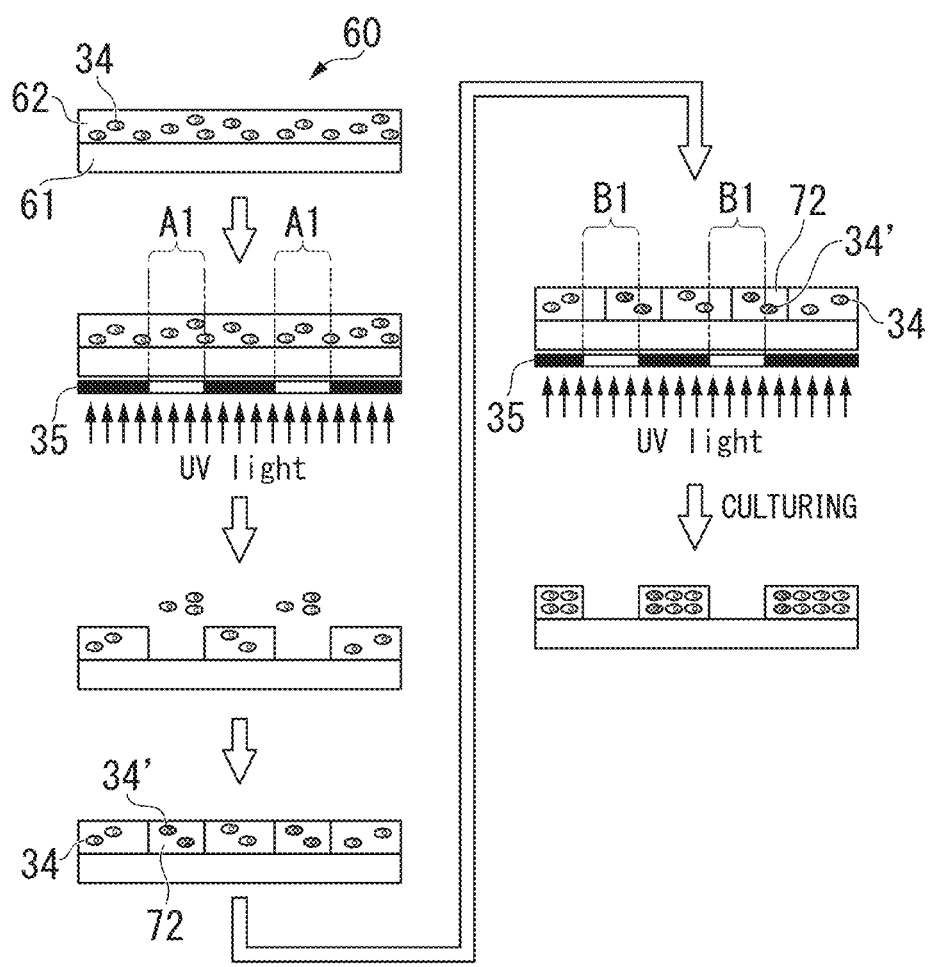

4-{4-[1-(9-Fluorenylmethyloxycarbonylamino)ethyl]-2-methoxy-5-nitrophenoxy}butanoic acid Depth=23.18μm(±5.88)

PHOTODEGRADABLE CROSS-LINKING AGENT, PHOTODEGRADABLE GEL, CELL CULTURE INSTRUMENT, CELL ARRANGEMENT-SORTING APPARATUS, CELL ARRANGEMENT METHOD, CELL SORTING METHOD, TISSUE FORMING METHOD, AND TISSUE

CROSS-REFERENCE TO RELATED APPLICATIONS

The present application is a 35 U.S.C. § § 371 national phase conversion of PCT/JP2014/062725, filed May 13, 2014, which claims priority to Japanese Patent Application No. 2013-108429, filed May 22, 2013, the contents of which are incorporated herein by reference. The PCT International Application was published in the Japanese language.

TECHNICAL FIELD

The present invention relates to a photodegradable cross-linking agent, which belongs to the field of material engineering and can be used particularly for manufacturing a complicated three-dimensional microtissue, and to a photodegradable gel, a cell culture instrument, a cell arrangement•sorting apparatus, a cell arrangement method, a cell sorting method, a tissue forming method, and a tissue which use the photodegradable cross-linking agent.

BACKGROUND ART

It is said that the cost for developing pharmaceutical products has exponentially increased in recent years in accordance with Eroom's law (NPL 1). Considering the fact that the probability of dropout of the development of pharmaceutical products at the clinical testing stage is increasing every year (NPL 2) or the problem of differences between species in animal testing, it is expected that in-vitro assay using cultured cells will be increasingly important in the future.

Currently, as a high-throughput system is becoming widespread, a cellular assay is widely used in a case of drug discovery screening. In recent years, a liquid handling technique such as an inkjet method has become usable, and hence the throughput is further increasing. Furthermore, there is a trend toward a high-content screening technique which makes it possible to obtain more information through a single assay.

However, in the monolayer culture used in the general cellular assay, the surrounding environment of the cell is greatly different from the internal environment of an animal, and this leads to a problem in that the cultured cell loses many of its functions which are supposed to be expressed in the body of the animal.

In next generation cellular assay techniques, an assay with higher reliability is adopted which uses a tissue having a higher function by artificially reconstructing a tissue imitating a three-dimensional structure in a biological body. Accordingly, an in vivo-in vitro correlation is expected to become stronger.

As one of the cell culture methods, there is a method of using a hydrogel. Due to the characteristics such as a high moisture content, ease of adjusting dynamic properties, and excellent nutrient diffusivity, the hydrogel is excellent as a cell carrier (NPL 3).

By the incorporation of a photodegradable group into the hydrogel molecule, the hydrogel obtains photodegradability, and in this way, a photodegradable gel which can be optically processed is developed. For example, there is a photodegradable gel which has polyethylene glycol as a main chain and contains a nitrobenzyl group in a molecule (PTL 1 and NPL 4). The physical properties of the hydrogel formed of a polymer monomer constituted as above can be controlled in terms of time and space by light irradiation (NPL 5 and 6), and the photodegradability is highly compatible with a living cell (NPL 4 and 7).

However, because the photodegradable gels reported so far are gelated by means of radical polymerization, they deteriorate in some cases by being influenced by oxygen when they are polymerized in the presence of oxygen. Furthermore, a radical damages cells or bioactive substances. In addition, because the polymer compound usable as a main chain is restricted to a polymer of a radically polymerizable monomer, there is a problem that the use thereof is limited.

The inventors of the present invention have developed a photodegradable cross-linking agent which can form a photodegradable gel by causing a cross-linking reaction simply by being mixed with a polymer compound without using radical polymerization (PTL 2).

REFERENCE LIST

Patent Literature (PTL)

[PTL 1] Japanese Unexamined Patent Application, First Publication No. 2007-108087
[PTL 2] Japanese Unexamined Patent Application, First Publication No. 2012-80844

Non-Patent Literature (NPL)

[NPL 1] Scannell, J. W. et. al., Nat. Rev. Drug Discov. (2012) Vol. 11, pp. 191-200.
[NPL 2] Pammolli, F. et. al., Nat. Rev. Drug Discov. (2011) Vol. 10, pp. 428-438.
[NPL 3] Drury, J. L. and Mooney, D. J., Biomaterials (2003) Vol. 24, pp. 4337-4351.
[NPL 4] Kloxin, A. M. et. al., Science (2009) Vol. 324, pp. 59-63.
[NPL 5] Kloxin, A. M. et. al., Adv. Mater. (2010) Vol. 22, pp. 61-66.
[NPL 6] Wong, D. Y. et. al., Macromolecules (2010) Vol. 43, pp. 2824-2831.
[NPL 7] Kloxin, A. M. et. al., Biomaterial (2010) Vol. 31, pp. 1-8.
[NPL 8] Kikuchi, K., et al., Biotechnol, Bioeng. (2009) Vol. 103, pp. 552.
[NPL 9] Nichol, J. W., et al., Biomaterials (2010) Vol. 31, pp. 5536.

SUMMARY OF THE INVENTION

Problems to be Solved by the Invention

The conventional photodegradable gel, which can be polymerized without using a radical polymerization reaction, swells by absorbing a solvent and thus collapses. Therefore, an intended structure cannot be constructed in some cases. Furthermore, there are problems in that the strength of the gel is poor, and it is difficult to prepare a complicated three-dimensional structure which can reproduce a biological structure. As a method for easily improving the strength of the gel, the concentration of the compound constituting the gel may be increased. However, if the concentration is increased, the moisture content of the gel is reduced. In addition, in a case in which the valency is kept constant so as to improve the strength of the gel, simply by reducing the molecular weight of the compound constituting the polymer, the strength of the gel can be improved, but the solubility of the gel in water is reduced. Consequently, it is difficult to handle the gel at the time of manufacturing and using it, and the state of the gel easily becomes ununiform.

The present invention has been made in consideration of the circumstances described above, and an object thereof is to provide a photodegradable cross-linking agent capable of manufacturing a photodegradable gel which has appropriate moisture content and water solubility as a cell carrier and has a strength that makes it possible to construct a complicated three-dimensional microstructure.

Another object of the present invention is to provide a photodegradable gel containing the photodegradable cross-linking agent, a cell culture instrument having the photodegradable gel, a cell arrangement•sorting apparatus using the cell culture instrument, a cell arrangement method and a cell sorting method using the cell culture instrument, and a tissue and a tissue forming method using the photodegradable gel.

Means for Solving the Problems

Through intensive research, the inventors of the present invention found that by increasing the number of branches of a photodegradable cross-linking agent, the strength of gel can be improved, and the aforementioned objects can be achieved, thereby completing the present invention. That is, the present invention is as follows.

[1] A photodegradable cross-linking agent including a polyethylene glycol main chain which has three or more branched chains and a photodegradable benzyl group which is disposed on the terminus of the polyethylene glycol main chain having the branched chains, in which the benzyl group has an active ester group, which is reactive with an amino group or a hydroxyl group, and one or more nitro groups in a benzene ring of the benzyl group.

[2] The photodegradable cross-linking agent described in [1], in which the active ester group is a derivative of N-hydroxysuccinimide.

[3] The photodegradable cross-linking agent described in [1] or [2], in which the average repetition number of ethylene glycol in the branched chains is within a range of 20 to 500.

[4] The photodegradable cross-linking agent described in any one of [1] to [3], in which the number of the branched chains is 4 or 8.

[5] The photodegradable cross-linking agent described in any one of [1] to [4], in which the polyethylene glycol main chain has a neopentyl skeleton.

[6] A photodegradable gel characterized in that it is obtained by reacting the photodegradable cross-linking agent described in any one of [1] to [5] with a polymer compound having a total of two or more amino groups or hydroxyl groups in a molecule, in which the amino groups or the hydroxyl groups in the polymer compound are cross-linked with the active ester group of the photodegradable cross-linking agent through condensation.

[7] The photodegradable gel described in [6], in which the polymer compound is at least one kind of compound selected from the group consisting of polyethylene glycol, polyvinyl alcohol, basic polysaccharide, a protein, and a derivative of any of these.

[8] The photodegradable gel described in [6] or [7], in which the polymer compound is a branched polyethylene glycol derivative.

[9] The photodegradable gel described in [6] or [7], in which the polymer compound is gelatin.

[10] A cell culture instrument in which a layer composed of the photodegradable gel described in any one of [6] to [9] is formed on the surface of a cell culture substrate.

[11] The cell culture instrument described in [10], in which at least the surface of the cell culture substrate is composed of a styrene-based resin or a cell-adhesive material.

[12] A cell arrangement•sorting apparatus including the cell culture instrument described in [10] or [11] and an irradiation portion irradiating the cell culture instrument with light, in which the irradiation portion has a light source and an irradiation area-adjusting portion which irradiates only a certain partial area of the surface of the cell culture instrument with the light from the light source.

[13] A cell sorting method including a step of irradiating only a partial area of the cell culture instrument described in [10] or [11] with light so as to selectively degrade the photodegradable gel of the partial area and to sort cells into cells of the partial area and cells in an area other than the partial area.

[14] A cell arrangement method including a step of irradiating only a partial area of the cell culture instrument described in [10] to [11] with light so as to selectively degrade the photodegradable gel of the partial area and to arrange cells in the partial region.

[15] A tissue forming method including (I) a step of forming the photodegradable gel described in [6]; (II) a step of specifying the shape of the photodegradable gel by light irradiation; (III) a step of seeding cells into the photodegradable gel; and (IV) a step of culturing the cells.

[16] A tissue forming method including (I) a step of forming the photodegradable gel described in [6] by embedding cells into the photodegradable gel; (II) a step of specifying the structure of the photodegradable gel by light irradiation; and (III) a step of culturing the cells.

[17] A tissue including the photodegradable gel described in any one of [6] to [9] and cells.

Effects of the Invention

According to the photodegradable cross-linking agent of the present invention, a photodegradable gel can be manufactured which has appropriate moisture content and water solubility as a cell carrier and has a strength that makes it possible to construct a complicated three-dimensional microstructure. Furthermore, a tissue having a complicated three-dimensional microstructure can be formed, and a highly reliable cellular assay system closer to a biological environment can be realized. Therefore, the present invention contributes to the progress of regenerative medical techniques and the development of novel pharmaceutical products.

BRIEF DESCRIPTION OF DRAWINGS

FIG. 9C is a schematic view showing a seventh example of the tissue forming method of the present invention.

EMBODIMENTS FOR CARRYING OUT THE INVENTION

<<Photodegradable Cross-Linking Agent>>

Figure 1:
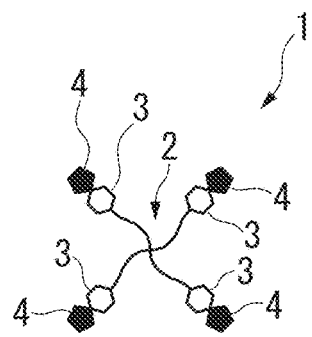
FIG. 1 is a schematic view of a photodegradable cross-linking agent of the present invention.

The photodegradable cross-linking agent of the present invention is a compound comprising a polyethylene glycol main chain which has 3 or more branched chains and a photodegradable benzyl group which is disposed on the terminus of the polyethylene glycol main chain, in which the benzyl group has an active ester group, which is reactive with an amino group or a hydroxyl group, and one or more nitro groups in a benzene ring of the benzyl group.

Examples of the photodegradable cross-linking agent include a compound represented by the following Formula (1).

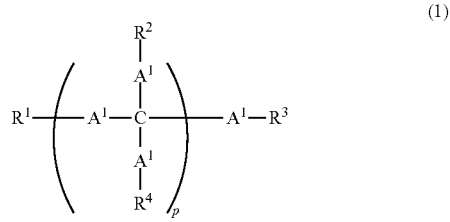

In Formula (1), each of $R^1$ to $R^4$ independently represents a hydrogen atom, Z, —O(CH$_2$CH$_2$O)$_n$—Z, or a linear or branched alkyl group having 1 to 20 carbon atoms.

Z represents a photodegradable benzyl group. The benzyl group has an active ester group, which is reactive with an amino group or a hydroxyl group, and one or more nitro groups in a benzene ring.

A plurality of $A^1$s represents a linking group. Each $A^1$ independently represents a single bond or a linear or branched alkyl group having 1 to 20 carbon atoms.

In the alkyl group, one —$CH_2$— group or each of two or more —$CH_2$— groups not being adjacent to each other may be independently substituted with —CH=CH—, —O—, —CO—, —COO—, —OCO—, or a cyclohexylene group.

p represents an integer of equal to or greater than 1, and a plurality of $R^2$s and $R^4$s may be the same as or different from each other. Among $R^1$ to $R^4$, at least 3 or more Rs contain Z, and 2 or more Rs represent —$O(CH_2CH_2O)_n$—Z.

The photodegradable cross-linking agent of the present invention has three or more branched chains. Therefore, plenty of cross-linking points are formed (per single molecule of the cross-linking agent) between the active ester group disposed on the terminus of the branched chain and the polymer compound reacting with the active ester group. Consequently, the photodegradable cross-linking agent of the present invention makes it possible to obtain a photodegradable gel having appropriate strength. Furthermore, the photodegradable cross-linking agent of the present invention has a group containing a photodegradable nitrobenzyl group. Accordingly, the photodegradable cross-linking agent of the present invention can be applied to optical microfabrication techniques represented by traditional photolithography or a two-photon excitation process which has been used in recent years. Thus, the photodegradable cross-linking agent of the present invention makes it possible to obtain a photodegradable gel which can be microfabricated by light irradiation. As a result, if the photodegradable cross-linking agent of the present invention is used, it is possible to construct a gel having a complicated three-dimensional microstructure.

An average repetition number n of ethylene glycol of the branched chains of polyethylene glycol contained in the photodegradable cross-linking agent represented by Formula (1) is within a range of 20 to 500, preferably within a range of 30 to 250, and even more preferably within a range of 40 to 125.

If the repetition number of ethylene glycol is set within the aforementioned range, the solubility of the gel in water can be improved. Therefore, it is easy to handle the gel at the time of manufacturing and using it and to obtain a uniform photodegradable gel.

In Formula (1), Z represents a photodegradable benzyl group. The benzyl group has an active ester group, which is reactive with an amino group or a hydroxyl group, and one or more nitro groups in a benzene ring.

The benzyl group is preferably a group represented by the following Formula (2) or (3).

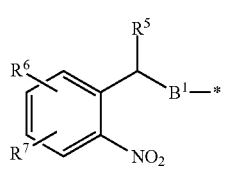

(2)

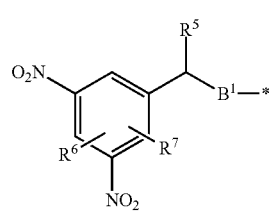

(3)

In Formulae (2) and (3), $B^1$ is a group represented by —$(CH_2)_m$—C(=O)—NH—, and m represents an integer of 0 to 5. m is preferably 5.

The asterisk represents a position where the compound is bonded to an oxygen atom of ethylene glycol.

$R^5$ represents hydrogen or a linear or branched alkyl group having 1 to 6 carbon atoms. $R^5$ is more preferably a linear alkyl group having 1 to 6 carbon atoms, and particularly preferably a methyl group. $R^6$ represents a linear or branched alkyl group having 1 to 6 carbon atoms or a linear or branched alkoxy group having 1 to 6 carbon atoms. $R^6$ is more preferably a linear alkoxy group having 1 to 6 carbon atoms, and particularly preferably a methoxy group. $R^7$ represents an active ester group which is reactive with an amino group or a hydroxyl group. $R^7$ is preferably a derivative of N-hydroxysuccinimide, and more preferably a derivative represented by the following Formula (4).

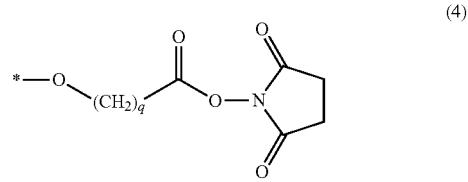

(4)

In Formula (4), the asterisk represents a position where the compound is bonded to a carbon atom of a benzene ring. q represents an integer of 1 to 10. q is preferably 1 to 6, more preferably 2 to 5, and particularly preferably 3.

Specifically, the compound represented by Formula (1) is preferably a compound represented by any of the following Formulae (7) and (8).

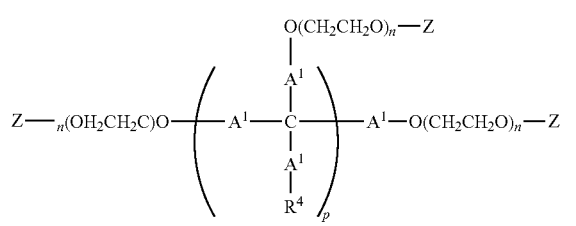

(7)

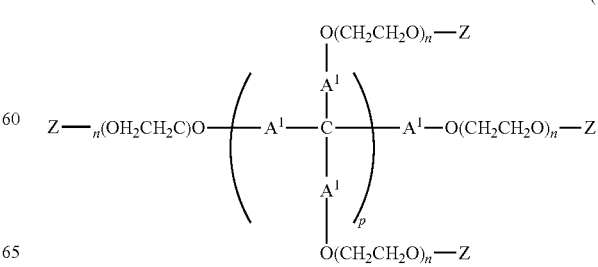

(8)

In Formulae (7) and (8), n, Z, $A^1$, $R^1$ to $R^4$, and p are the same as those in Formula (1).

Specifically, when p is 1, the compound represented by Formula (1) is preferably a compound represented by the following Formula (9).

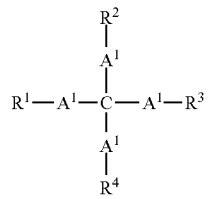
(9)

In Formula (9), Z, $A^1$, and $R^1$ to $R^4$ are the same as those in Formula (1).

Specifically, the compound represented by Formula (9) is preferably a compound represented by the following Formula (10) or (11).

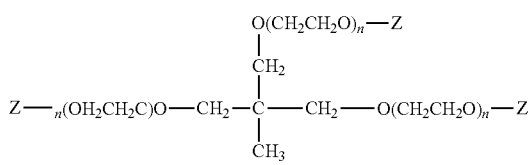
(10)

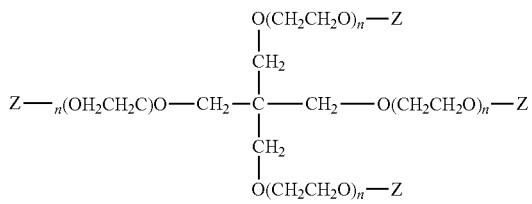
(11)

In Formulae (10) and (11), n and Z are the same as those in Formula (1).

Specifically, the compound represented by Formula (1) is preferably a compound represented by the following Formula (12).

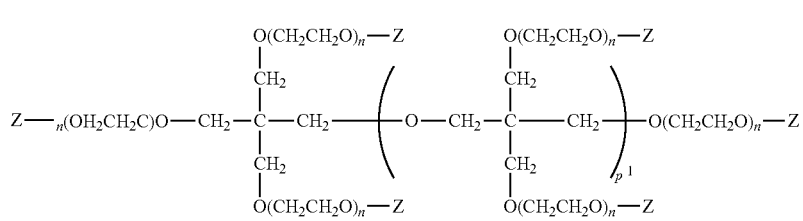
(12)

In Formula (12), Z is the same as Z in Formula (1). $p^1$ represents an integer of equal to or greater than 1.

Specifically, the compound represented by Formula (12) is preferably a compound represented by the following Formula (13) or (14).

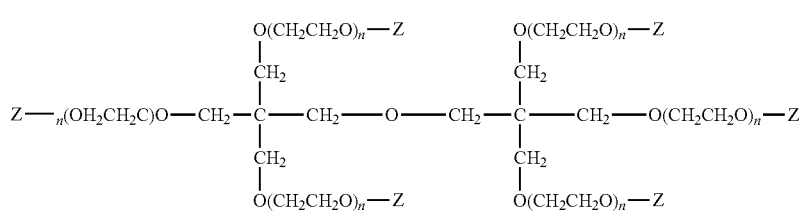
(13)

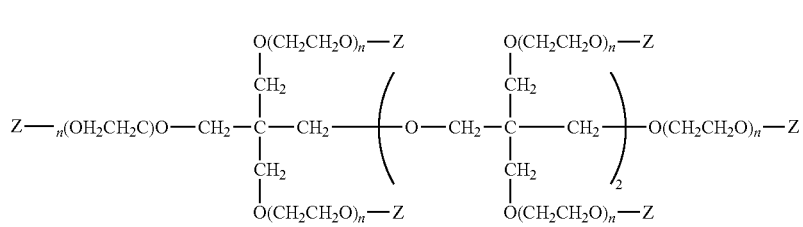
(14)

In Formulae (13) and (14), n and Z are the same as those in Formula (1).

The 4-arm branched or 8-arm branched polyethylene glycol (or a derivative thereof) is easily synthesized and readily available. Therefore, the polyethylene glycol in the compound represented by Formula (1) is preferably 4-arm branched or 8-arm branched (the number of the branched chains is 4 or 8).

That is, the photodegradable cross-linking agent of the present invention is more preferably a compound represented by the following Formula (15) or (16).

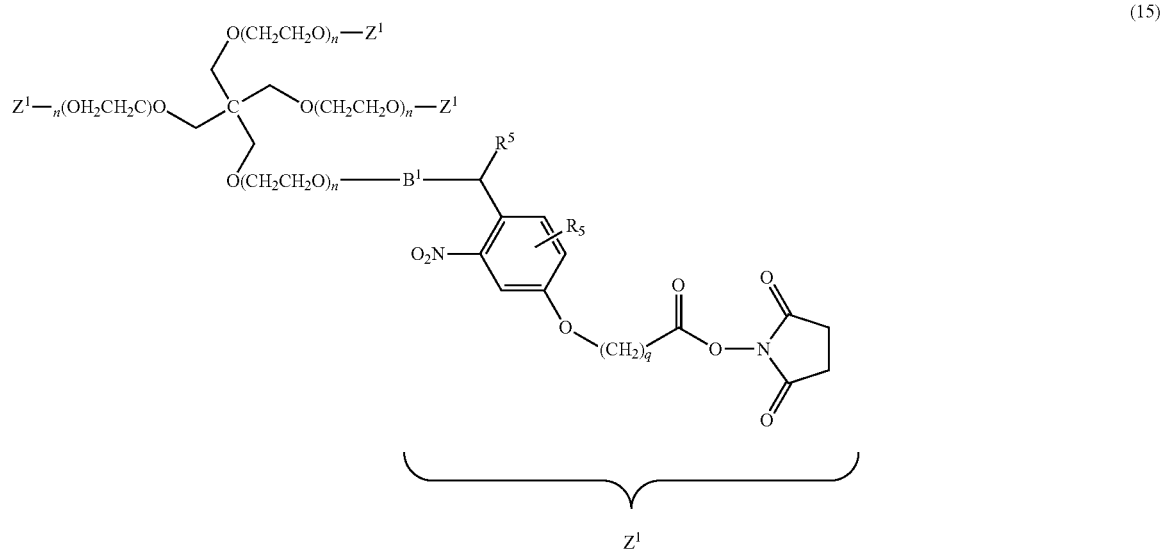

(15)

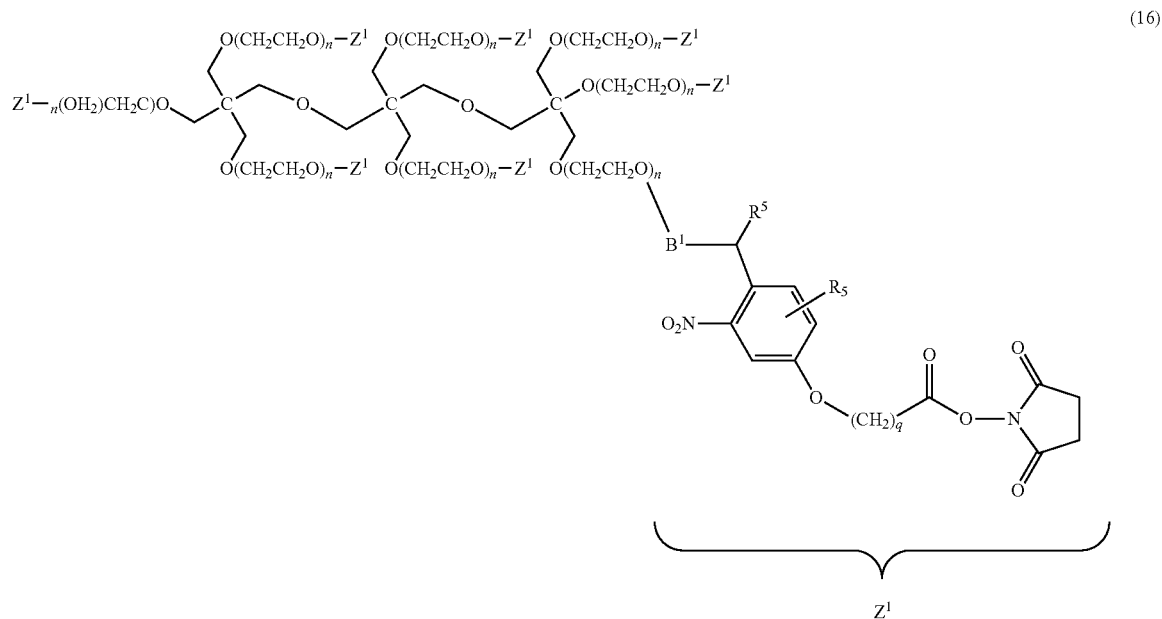

(16)

In Formulae (15) and (16), $B^1$, $R^5$, $R^6$, and q are the same as those in Formulae (2) to (4).

Specifically, the compound represented by Formula (15) or (16) is more preferably a compound represented by the following Formula (17) or (18).

an active ester group 4 which is disposed on the terminus of the nitrobenzyl group-containing group 3. The photodegradable cross-linking agent 1 has 4-arm branched polyethylene glycol chains, and the branched chains of polyethylene glycol have a neopentyl skeleton at the center.

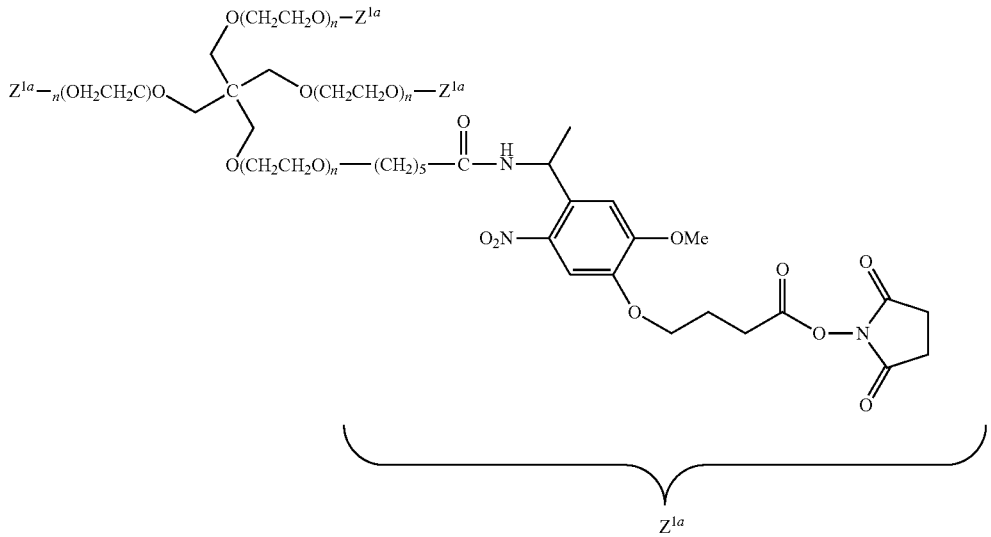

(17)

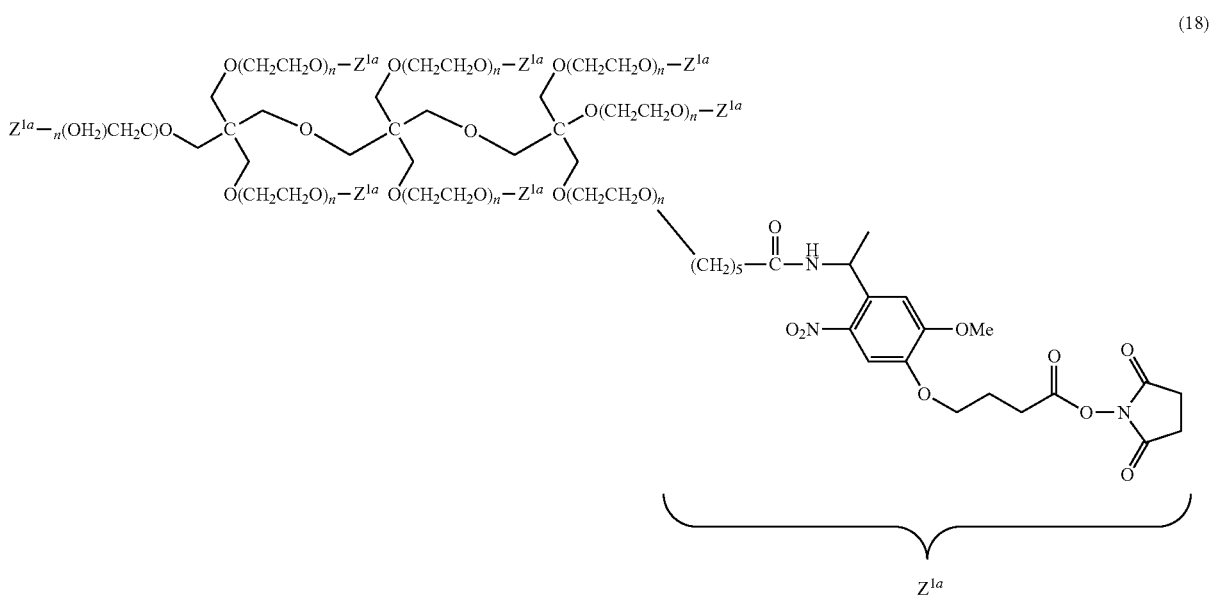

(18)

The polyethylene glycol preferably has a neopentyl skeleton, and is particularly preferably a compound represented by Formula (17) or (18).

Figure 2:
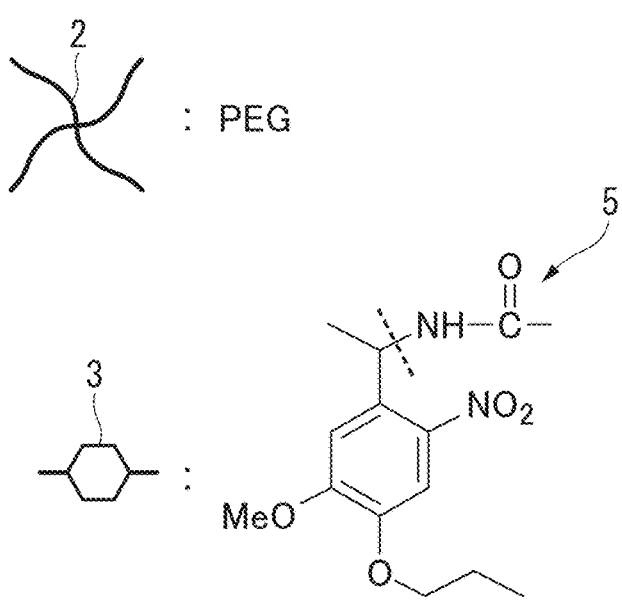
FIG. 2 is a view showing the structure of the photodegradable cross-linking agent of the present invention.
Figure 2:
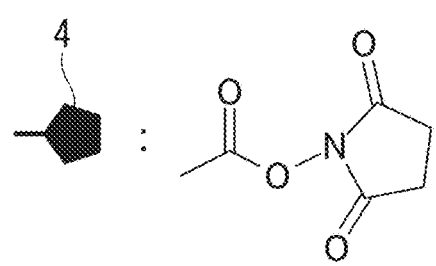

FIG. 1 is a schematic view of the compound represented by Formula (17). As shown in FIG. 1, a photodegradable cross-linking agent 1 contains a main chain 2 which is composed of branched polyethylene glycol (PEG), a photodegradable nitrobenzyl group-containing group 3 which is disposed on the terminus of the branched main chain 2, and As shown in FIGS. 1 and 2, the main chain 2 is polyethylene glycol (PEG), and the nitrobenzyl group-containing group 3 is bonded to the main chain 2 through an amide bond portion 5 (—NHCO—).

<<Synthesis of Photodegradable Cross-Linking Agent>>

The method for manufacturing the compound represented by Formula (1) will be described.

The compound represented by Formula (1) is a compound having a polyethylene glycol main chain, which has 3 or more branched chains, and a photodegradable benzyl group which is disposed on the terminus of the branched chains, in which the benzyl group has an active ester group, which is reactive with an amino group or a hydroxyl group, and one or more nitro groups in a benzene ring of the benzyl group. Hereinafter, a reaction will be described in which the photodegradable benzyl group is disposed on the terminus of the branches, and the active ester group is disposed in the benzyl group.

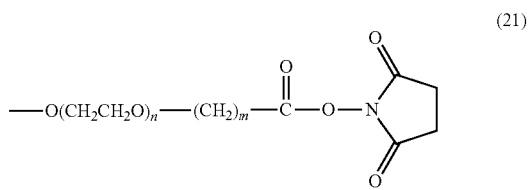

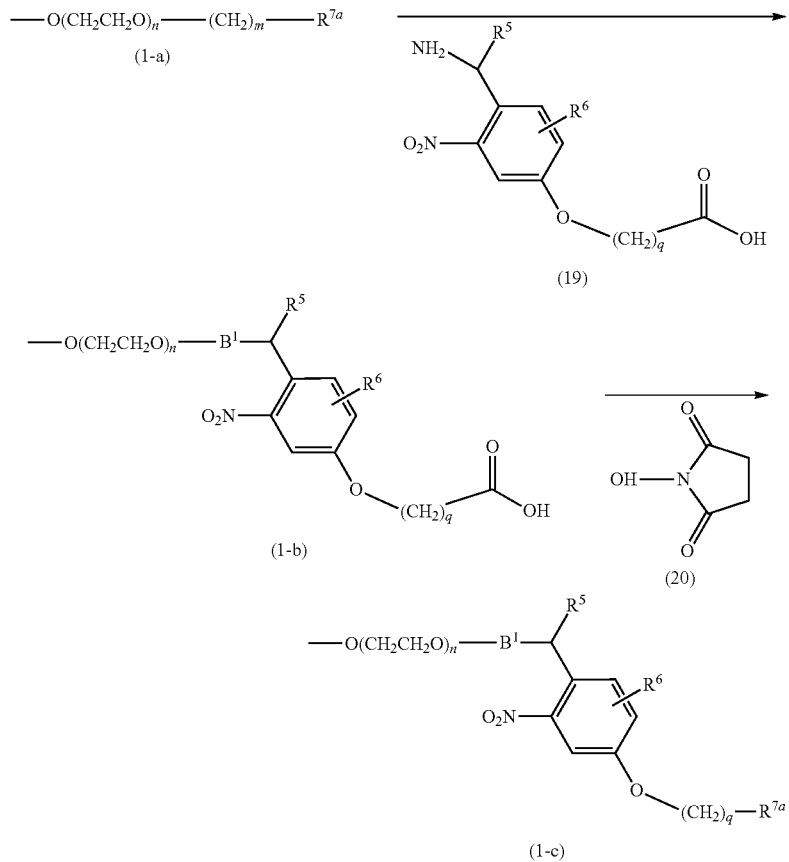

In the formulae, $B^1$, $R^5$, $R^6$, and q are the same as those in Formulae (2) to (4). $R^{7a}$ represents an active ester group which is reactive with an amino group or a hydroxyl group.

A group represented by Formula (1-c) is obtained as below. A group represented by Formula (1-a) and a compound represented by Formula (19) in a molar amount that is 1.0 to 2.0 times the molar amount of the compound represented by Formula (1-a) are treated in a solvent for tens of minutes to 24 hours at a temperature of 0° C. to 200° C., and the solvent is removed. Then, a compound represented by Formula (1-b) is precipitated and purified. Thereafter, the resultant and a compound represented by Formula (20) in a molar amount that is 1.0 to 2.0 times greater than the molar amount of the compound represented by Formula (1-b) are treated in a solvent for tens of minutes to 24 hours at a temperature of 0° C. to 200° C. in the presence of a catalyst, and from the resultant, the compound (1-c) is isolated. As the catalyst, 1-ethyl-3-(3-dimethylaminopropyl)carbodiimide hydrochloride (EDC) is preferable.

The group represented by Formula (1-a) is preferably a compound represented by the following Formula (21).

In Formula (21), n and m are the same as those in Formulae (1) to (3).

The group represented by Formula (1-c) is preferably a compound represented by the following Formula (22).

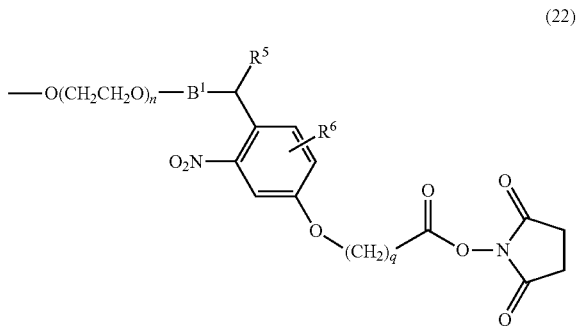

In Formula (22), n, $B^1$, $R^5$, $R^6$, and q are the same as those in Formulae (1) to (4).

<<Photodegradable Gel>>

The photodegradable gel of the present invention is obtained by reacting the photodegradable cross-linking agent of the present invention with a polymer compound which has a total of 2 or more amino groups or hydroxyl groups in a molecule, in which the amino groups or hydroxyl groups of the polymer compound are cross-linked with the active ester group of the photodegradable cross-linking agent through condensation.

The polymer compound is preferably at least one kind of compound selected from the group consisting of polyethylene glycol, polyvinyl alcohol, basic polysccharide, a protein, and a derivative of any of these.

The polymer compound is more preferably branched polyethylene glycol or a derivative thereof. Alternatively, the polymer compound is more preferably gelatin as a protein.

As the polymer compound, polyethylene glycol is preferable because it seldom interacts with a cell and can dissolve in water. Especially, it is preferable to use branched polyethylene glycol or a derivative thereof because a network structure is easily formed and gelation easily proceeds. The number of branches of the branched polyethylene glycol (or a derivative thereof) is preferably equal to or greater than 3. Especially, 4-arm branched polyethylene glycol (or a derivative thereof) is preferable because it is readily available.

It is desirable that the polyethylene glycol (or a derivative thereof) has an amino group on the terminus thereof.

The molecular weight of the polyethylene glycol (or a derivative thereof) is preferably within a range of 10,000 to 40,000.

Collagen as a main component of gelatin is the main component of an extracellular matrix of multicellular organisms (animals). Therefore, collagen is preferable as a scaffolding protein of a cell. Furthermore, collagen is preferable because it promotes the growth and differentiation of a cell in some cases. The type of the collagen used is not particularly limited, but it is preferable to use a type A gelatin obtained by treating a raw material derived from cow skin or pig skin with an acid.

The strength of gelatin is not particularly limited. However, it is preferably 200 Bloom to 400 Bloom and more preferably 250 Bloom to 350 Bloom.

As the basic polysaccharide, chitosan is preferable.

When the polymer compound is mixed with the photodegradable cross-linking agent, the amino groups or hydroxyl groups of the polymer compound are cross-linked with the active ester group of the photodegradable cross-linking agent through condensation.

The amino group forms an amide bond with the active ester group of the photodegradable cross-linking agent, and the hydroxyl group forms an ester bond with the active ester group. As a result, a network structure is formed, gelation proceeds, and a photodegradable gel is generated.

In the present invention, an additive for accelerating the cross-linking reaction is not particularly required. Accordingly, simply by mixing the polymer compound with the photodegradable gel, the cross-linking reaction occurs, and gelation proceeds. Furthermore, the reaction may be performed at room temperature.

In the present invention, the cross-linking reaction is not influenced by dissolved oxygen, and hence a thin film-like gel is easily formed.

The amount of the photodegradable cross-linking agent added to the polymer compound (photodegradable cross-linking agent/polymer compound) can be freely set within a range in which gelation occurs. However, in order to prepare a gel with high strength, a molar ratio of the active ester group of the photodegradable cross-linking agent to the amino group of the polymer compound is preferably about 1:1. For example, when 4-arm branched polyethylene glycol (or a derivative thereof) having an amino terminus is used as the polymer compound, and a 4-arm branched photodegradable cross-linking agent is used, a mixing ratio (polymer compound:photodegradable cross-linking agent) between the polymer compound and the photodegradable cross-linking agent is preferably within a range of 4:1 to 1:4, and more preferably within a range of 2:1 to 1:2.

When 4-arm branched polyethylene glycol (or a derivative thereof) is used as the polymer compound, the amount thereof used is preferably set such that the amount of the polyethylene glycol contained in the photodegradable gel becomes equal to or greater than 2.5% by weight. When gelatin is used as the polymer compound, the amount thereof used is preferably set such that the amount of gelatin contained in the photodegradable gel becomes equal to or greater than 1.0% by weight.

Figure 3A:
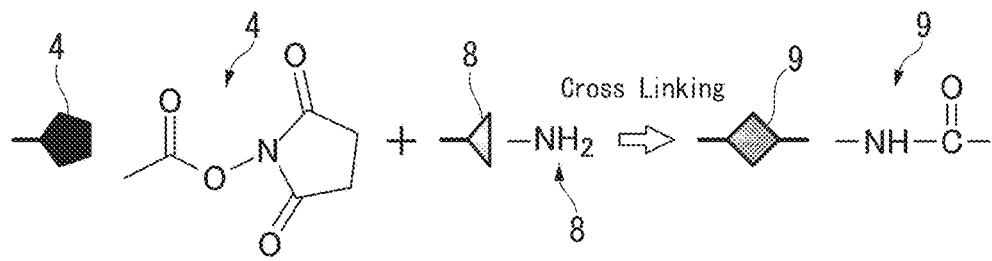
FIG. 3A is a view showing a reaction of generating a photodegradable gel of the present invention.

FIG. 3A is a view showing a reaction in which an active ester group 4 disposed on the terminus of a photodegradable cross-linking agent 1 is cross-linked with an amino group 8 of the polymer compound by forming an amide bond 9 through condensation.

Figure 3B:
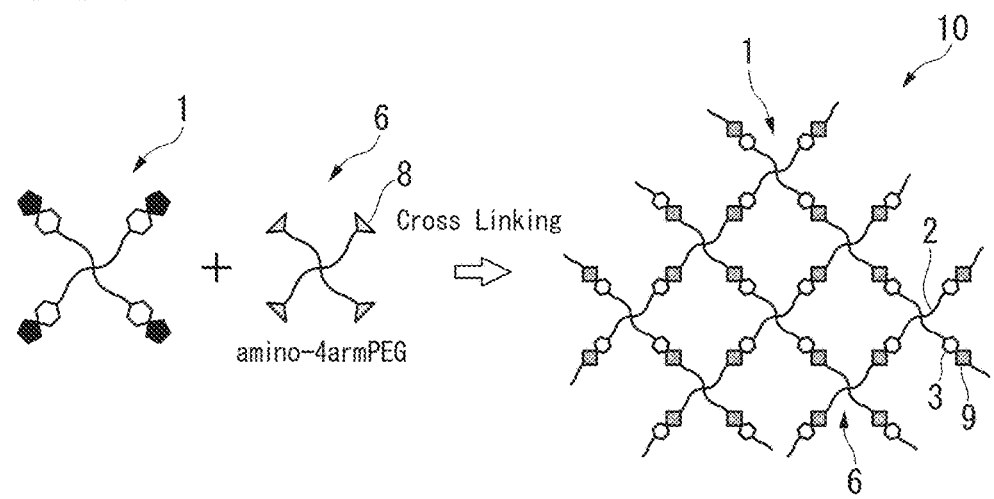
FIG. 3B is a view showing a state in which a photodegradable gel according to an embodiment of the present invention is generated by a reaction between the photodegradable cross-linking agent and a polyethylene glycol derivative.

FIG. 3B is a view schematically showing a reaction in which a photodegradable gel 10 is generated by reacting the photodegradable cross-linking agent with a polymer compound 6.

The polymer compound 6 is a 4-arm branched polyethylene glycol derivative having the amino group 8 on the terminus.

When the polymer compound 6 is mixed with the photodegradable cross-linking agent 1, the amino group of the polymer compound 6 is cross-linked with the active ester group 4 of the photodegradable cross-linking agent 1 through condensation.

As a result, the polymer compound 6 is bonded to another polymer compound 6 through the photodegradable cross-linking agent 1, and thus the photodegradable gel 10 having a network structure is generated.

Figure 3C:
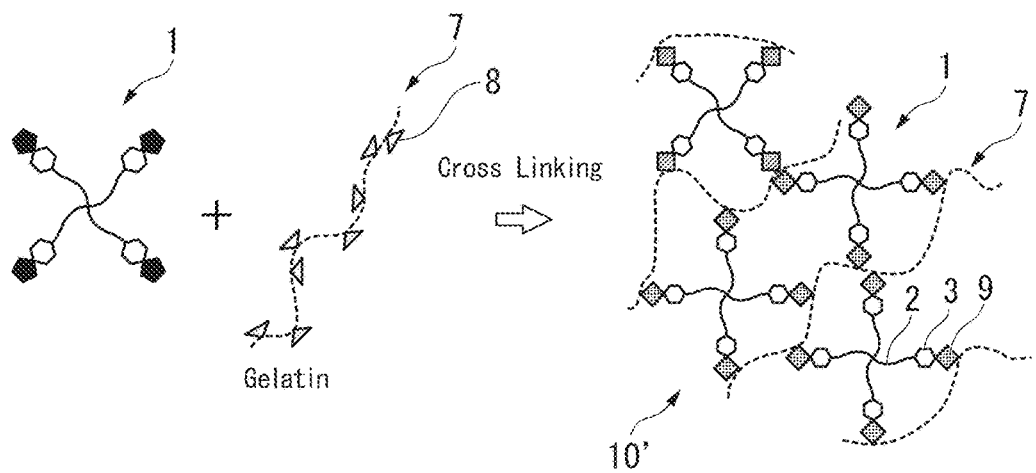
FIG. 3C is a view showing a state in which a photodegradable gel according to another embodiment of the present invention is generated by a reaction between the photodegradable cross-linking agent and gelatin.

FIG. 3C is a view schematically showing a reaction in which a photodegradable gel 10' is generated by reacting the photodegradable cross-linking agent with a polymer compound 7.

The polymer compound 7 is gelatin having the amino group 8 in a molecule.

When the polymer compound 7 is mixed with the photodegradable cross-linking agent 1, an amino group of the polymer compound 7 is cross-linked with the active ester group 4 of the photodegradable cross-linking agent 1 through condensation.

As a result, the polymer compound 7 is bonded to another polymer compound 7 through the photodegradable cross-linking agent 1, and thus the photodegradable gel 10' having a network structure is generated.

The photodegradable gel of the present invention is degraded by the degradation of the photodegradable cross-linking agent 1 through light irradiation.

Figure 4A:
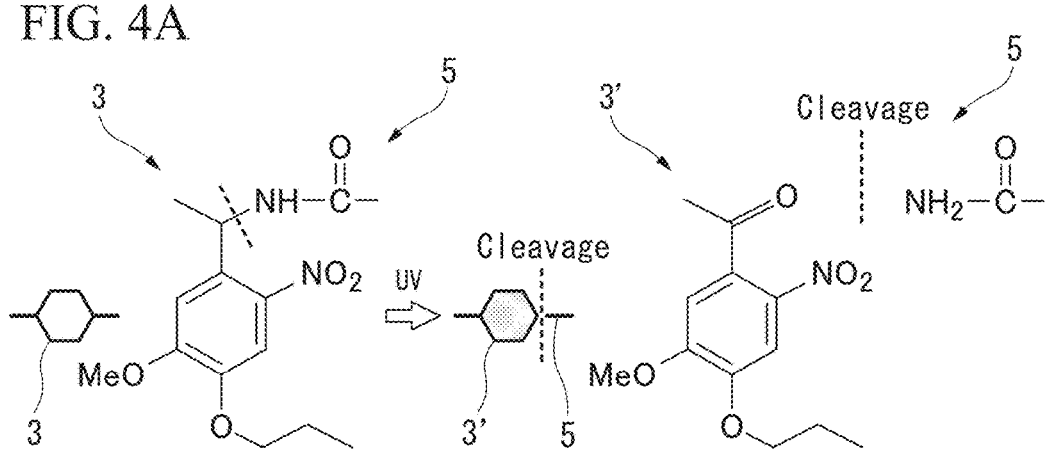
FIG. 4A is a view showing a reaction of degrading the photodegradable gel of the present invention.

FIG. 4A is a view showing the way a nitrobenzyl group of the photodegradable cross-linking agent is degraded. In the position indicated by a broken line, a nitrobenzyl group-containing group 3 can be degraded by being irradiated with light such as ultraviolet rays having a wavelength of 330 nm to 380 nm.

When a bond between the nitrobenzyl group-containing group 3 and an amino group of an amide bond portion 5 is cleaved, the nitrobenzyl group-containing group 3 turns into a nitrobenzyl group 3'. Herein, depending on the structure of the nitrobenzyl group, a bond between the nitrobenzyl group-containing group 3 and the active ester group 4 is cleaved by the light irradiation described above.

Figure 4B:
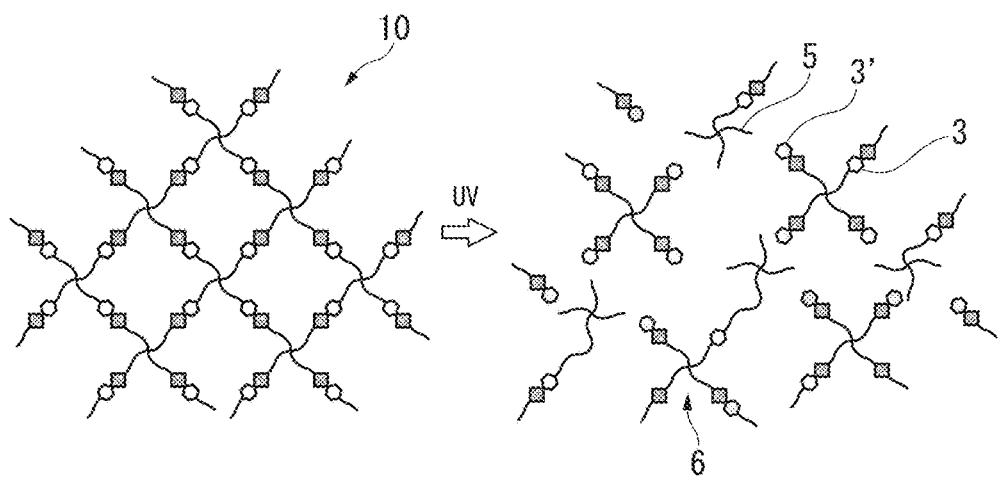
FIG. 4B is a view schematically showing the way a photodegradable gel according to an embodiment of the present invention is degraded by light irradiation.
Figure 4C:
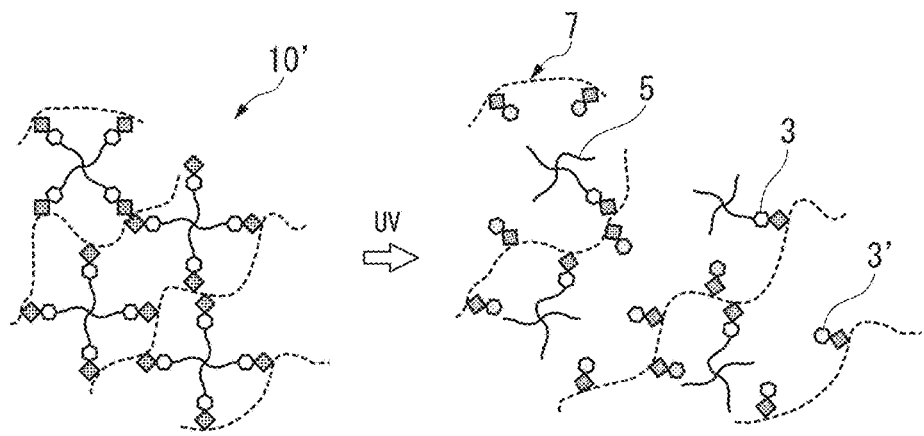
FIG. 4C is a view schematically showing the way a photodegradable gel according to another embodiment of the present invention is degraded by light irradiation.

Each of FIGS. 4B and 4C is a view schematically showing the way the photodegradable gels 10 and 10' are degraded by the light irradiation. As a result of the degradation, the photodegradable gel dissolves in water.

According to the present invention, because the photodegradable cross-linking agent having the structure described above is used, a cross-linking reaction occurs simply by mixing the photodegradable cross-linking agent with the polymer compound, and thus gelation proceeds.

In the conventional manufacturing process of a photoresponsive gel and a photodegradable gel in which gelation is caused by means of radical polymerization, if there is oxygen at the time of the polymerization, the polymerization reaction is hindered, and gelation does not proceed. This phenomenon becomes marked particularly at the time of preparing a thin film-like gel. However, if the photodegradable cross-linking agent of the present invention is used, the cross-linking reaction is not at all influenced by oxygen. Therefore, the polymerization reaction is not hindered as described above.

Even when a radical polymerization reaction is used, if the reaction is performed under the condition of an oxygen-free atmosphere, it may be possible to prepare a thin film-like gel. However, in such a case, it is necessary to use facilities for performing the polymerization reaction under an oxygen-free condition, and thus the manufacturing process becomes complicated.

In contrast, if the photodegradable cross-linking agent of the present invention is used, the condition of the oxygen-free atmosphere is not required. Accordingly, the manufacturing process of a thin film-like gel is simplified, and it is possible to efficiently prepare a photodegradable gel at low cost.

Furthermore, in the present invention, a radical polymerization is not used for the cross-linking reaction. Accordingly, it is possible to prepare a photodegradable gel in a state in which substances that are easily damaged by a radical are mixed together. Consequently, the photodegradable gel can be used for various purposes, for example, for the purpose of immobilizing cells or bioactive substances. In addition, a polymer of a monomer which cannot be subjected to radical polymerization can also be used as a polymer compound. Therefore, the present invention is advantageous because a wide range of polymer compounds can be selected.

The photodegradable gel of the present invention has appropriate strength and photodegradability. Therefore, the photodegradable gel of the present invention can be applied to optical microfabrication techniques represented by traditional photolithography or a two-photon excitation process which has been used in recent years. Furthermore, the photodegradable gel of the present invention can achieve appropriate moisture content as a cell carrier while having appropriate strength. Accordingly, the photodegradable gel of the present invention is an extremely useful material because it can be used as a cell carrier having a complicated three-dimensional microstructure.

<<Cell Culture Instrument>>

In a cell culture instrument of the present invention, a layer composed of the photodegradable gel of the present invention is formed on the surface of a cell culture substrate.

The thickness of the photodegradable gel layer is preferably 100 nm to 100 μm, more preferably 300 nm to 30 μm, and particularly preferably 1,000 nm to 10 μm.

The material constituting the cell culture substrate is not particularly limited, and examples thereof include plastic, glass, modified glass, a metal, and the like.

As plastic, a styrene-based resin (for example, polystyrene (PS)), an acrylic resin (for example, a polymethyl methacrylate (PMMA) resin), a polyvinylpyridine-based resin (poly(4-vinylpyridine), a 4-vinylpyridine-styrene copolymer, or the like), a silicone-based resin (for example, a polydimethylsiloxane resin), a polyolefin-based resin (for example, a polyethylene resin, a polypropylene resin, or a polymethylpentene resin), a polyester resin (polyethylene terephthalate (PET) resin), a polycarbonate-based resin, an epoxy resin, and the like are preferable.

As the cell culture substrate, a substrate is preferable which has the same structure as that of a cell culture dish or a microplate that are generally used for cell culturing.

It is preferable that at least the surface of the cell culture substrate is composed of polystyrene or a cell-adhesive material.

As the cell-adhesive material, a cell-adhesive protein or a cell-adhesive peptide is preferable.

The cell-adhesive protein is preferably at least one kind of protein selected from the group consisting of fibronectin, collagen, gelatin, and laminin, and particularly preferably gelatin. The cell-adhesive peptide preferably has an amino acid sequence consisting of arginine-glycine-aspartate (RGD sequence).

In the cell culture instrument of the present invention, a layer composed of the photodegradable gel of the present invention is formed on the surface of a cell culture substrate. The photodegradable gel of the present invention is a material preferable as a cell carrier which can construct a complicated three-dimensional microstructure. By using the photodegradable gel of the present invention alone, cells can be cultured, and the gel can be processed. However, if the photodegradable gel of the present invention is formed on the surface of a cell culture substrate, the culturing of cells and the process of the gel become easier.

<<Cell Arrangement•Sorting Apparatus>>

Figure 5:
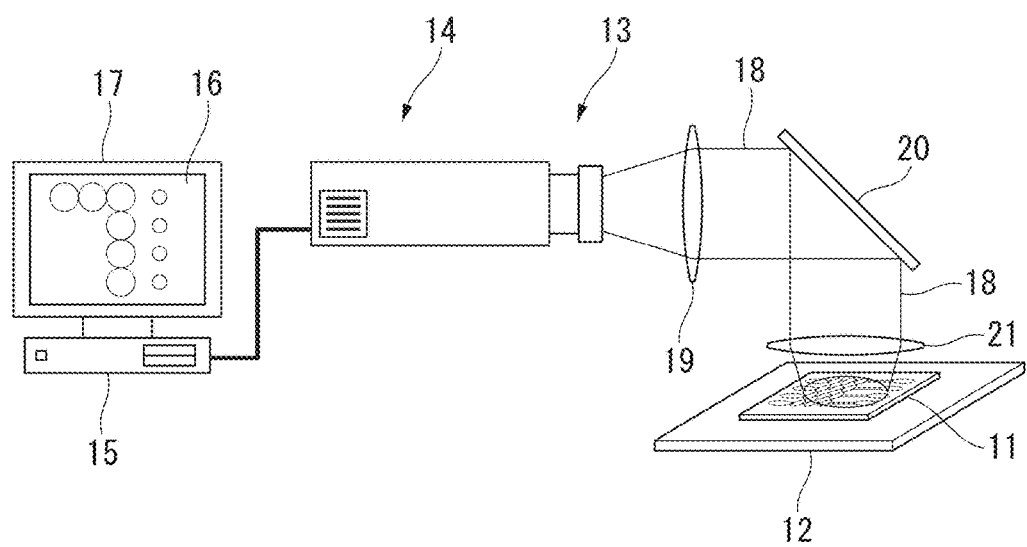
FIG. 5 is a schematic view showing an example of the constitution of a cell arrangement•sorting apparatus of the present invention.

FIG. 5 shows an example of a cell arrangement•sorting apparatus of the present invention. In FIG. 5, the apparatus includes a holding stand 12 which holds a cell culture instrument 11 and an irradiation portion 13 which irradiates the cell culture instrument 11 with light.

The irradiation portion 13 has a light source (not shown in the drawing), an irradiation area-adjusting portion 14 which irradiates only a certain partial area of the cell culture instrument 11 with light, and a control portion 15 such as a personal computer.

The irradiation area-adjusting portion 14 can irradiate the cell culture instrument 11 with light which forms a predetermined pattern 16. The pattern 16 is displayed on a display device 17.

The irradiation area-adjusting portion 14 includes, for example, a Digital Micromirror Device (DMD). DMD has a plurality of micromirrors, and each of the micromirrors is disposed such that the angle thereof can be independently set according to a signal from the control portion 15. By reflecting light from the light source, the micromirrors enable the cell culture instrument 11 to be irradiated with light 18 forming a pattern according to the signal.

Through a lens 19, a mirror 20, and a lens 21, the irradiation area-adjusting portion 14 can irradiate a certain area of the cell culture instrument 11 with light 18. The irradiation area-adjusting portion 14 can irradiate only a partial area of the cell culture instrument 11 with the light 18 in a certain shape or can irradiate the entire area of the cell culture instrument 11 with the light 18.

As the light source, those that can degrade the photodegradable cross-linking agent are selected. For example, it is possible to use light sources (for example, an ultraviolet lamp and a visible light lamp) that can radiate light such as ultraviolet rays and visible light.

The wavelength band of the light is, for example, 200 nm to 1,000 nm. The wavelength band is preferably 300 nm to 600 nm and particularly preferably 350 nm to 400 nm. The irradiation energy is generally 0.01 J/cm$^2$ to 1,000 J/cm$^2$, preferably 0.1 J/cm$^2$ to 100 J/cm$^2$, and more preferably 1 J/cm$^2$ to 10 J/cm$^2$.

The constituent for irradiating only a partial area of the cell culture substrate with light is not limited to DMD, and it is possible to adopt a liquid crystal shutter array, an optical spatial modulation element, a photomask in a predetermined shape, and the like.

As will be described later, the cell arrangement•sorting apparatus shown in FIG. 5 can be used as a cell arrangement apparatus for arranging cells in a partial area irradiated with light and as a sorting apparatus for sorting cells into cells in the area irradiated with light and cells in other areas.

The photodegradable gel of the present invention is a material which can construct a complicated three-dimensional microstructure by light irradiation and can be used as a cell carrier. Accordingly, if the cell arrangement•sorting apparatus of the present invention is combined with an optical microfabrication technique and a cell culture technique, cells can be three-dimensionally arranged, cultured, and sorted with high accuracy. Furthermore, because cells can be arranged, cultured, and sorted simultaneously, it is possible to sort and arrange cells while ascertaining the three-dimensional state of the cells.

<<Cell Arrangement and Sorting Method>>

Next, a cell sorting method will be described which includes a step of irradiating only a partial area of the cell culture instrument with light by using the cell culture instrument of the present invention so as to selectively degrade the photodegradable gel of the partial area and to sort cells into cells in the partial area and cells in an area other than that (the partial area). Furthermore, a cell arrangement method including a step of arranging cells in the partial area will be described.

In the present invention, the cells to be sorted are not particularly limited. According to the purpose, it is possible to use cells derived from animals (for example, human cells), cells derived from plants, cells derived from microorganisms, and the like.

Specific examples of the cells include somatic stem cells such as hematopoietic stem cells, myeloid stem cells, neural stem cells, and dermal stem cells; embryonic stem cells; and artificial multipotent stem cells.

In addition, white blood cells such as neutrophils, eosinophils, basophils, monocytes, lymphocytes (T cells, NK cells, B cells, and the like), hemocytes such as thrombocytes, red blood cells, vascular endothelial cells, lymphoid stem cells, erythroblasts, myeloblasts, monoblasts, megakaryoblasts, and megakaryocytes; endothelial cells, epithelial cells, liver parenchymal cells, cells of the islets of Langerhans, and various cell strains established for research purposes can be the target of the present invention.

In the present invention, the attachment (adhesion) of a cell means a state in which the cell does not move from its position even when a certain physical stimulus such as washing with a culture medium, a buffer solution, or the like is given to the cell. For example, a state in which a cell does not move even when being washed by the flow of a culture medium, a buffer solution, or the like at a predetermined shear stress (for example, 0.1 N/m$^2$ to 10 N/m$^2$) can be regarded as an "adhesion state" (attachment state).

The cell arrangement and sorting method of the present invention is a method of selectively degrading the photodegradable gel of a partial area by irradiating only the partial area of the cell culture instrument. In this method, the photodegradable gel is also processed while being degraded. When the vertical and horizontal directions (XY-axis direction) of the photodegradable gel layer are focused on, by the selective degradation of the photodegradable gel, the photodegradable gel is two-dimensionally processed. When the thickness direction (Z-axis direction) of the photodegradable gel layer is focused on, the photodegradable gel is three-dimensionally processed.

Within the photodegradable gel layer included in the portion irradiated with light, the entirety of the gel may be degraded. Alternatively, only the degradation depth in the Z-axis direction can be arbitrarily changed without degrading the entirety of the gel.

(Cell Arrangement Method)

Figure 6A:
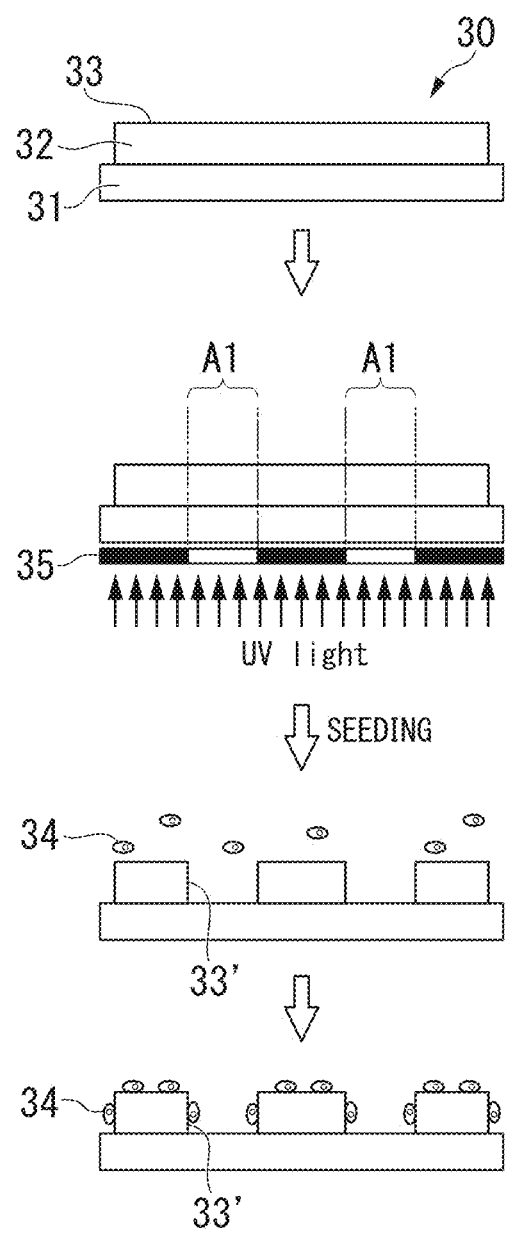
FIG. 6A is a schematic view showing an example of a cell arrangement method of the present invention.

Hereinafter, a first exemplary cell arrangement method will be specifically described with reference to FIG. 6A. FIG. 6A is a schematic view of a cell culture instrument 30.

A photodegradable gel layer 32 is formed on the surface of a cell culture substrate 31. The surface of the cell culture substrate 31 is preferably a material having low cell adhesiveness, such as glass or a silicone-resin. The photodegradable gel layer preferably exhibits high cell adhesiveness, and the polymer compound cross-linked with the photodegradable cross-linking agent of the present invention contained in the photodegradable gel layer is preferably the cell-adhesive protein described above.

The photodegradable gel layer 32 may be a mixed material in which the photodegradable gel is mixed with the cell-adhesive material.

An area A1 as a portion of the photodegradable gel layer 32 of the cell culture instrument 30 is irradiated with light through a photomask 35, thereby degrading the photodegradable gel layer 32 of the area A1. The photodegradable gel of the area A1 is solubilized and removed from the surface of the cell culture substrate 31 by washing. In this way, the photodegradable gel layer 32 is three-dimensionally processed.

When being seeded into the cell culture instrument 30, the cells 34 adhere only to a surface 33 of the photodegradable gel layer 32 and a surface 33' of the photodegradable gel layer that is newly formed by the light irradiation.

The cells 34 which have not adhered to the surfaces 33 and 33' of the photodegradable gel layer 32 can be removed from the cell culture instrument 30 by being washed with a culture medium, a buffer solution, or the like. In this way, it is possible to selectively arrange the cells 34 on the three-dimensionally processed photodegradable gel layer 32.

Figure 6B:
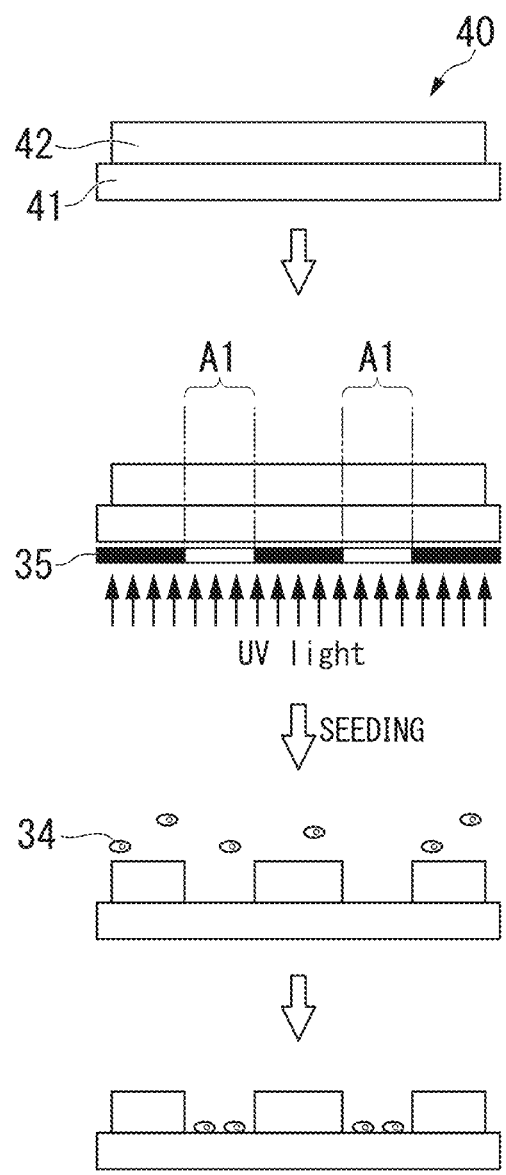
FIG. 6B is a schematic view showing another example of the cell arrangement method of the present invention.

Hereinafter, a second exemplary cell arrangement method will be specifically described with reference to FIG. 6B. FIG. 6B is a schematic view of a cell culture instrument 40.

A photodegradable gel layer 42 is formed on the surface of a cell culture substrate 41. The surface of the cell culture substrate 41 is preferably a material having high cell adhesiveness, such as polystyrene. When the surface of the cell culture substrate 41 does not contain a cell-adhesive material, a coating layer composed of a cell-adhesive material may be formed on the cell culture substrate 41.

The photodegradable gel layer 42 preferably has low cell adhesiveness. The polymer compound cross-linked with the photodegradable cross-linking agent of the present invention contained in the photodegradable gel layer 42 is preferably at least one kind of compound selected from the group consisting of polyethylene glycol, polyvinyl alcohol, basic polysaccharide, a protein having low cell adhesiveness, and a derivative of any of these. The polymer compound is particularly preferably a derivative of branched polyethylene glycol.

The area A1 as a portion of the photodegradable gel layer 42 of the cell culture instrument 40 is irradiated with light through the photomask 35, thereby degrading the photodegradable gel layer 42 of the area A1. The photodegradable gel of the area A1 is solubilized and removed from the surface of the cell culture substrate 41 by washing.

When being seeded into the cell culture instrument 40, the cells 34 adhere only to the surface of the cell culture substrate 41 of the area A1 from which the photodegradable gel layer 42 has been removed.

The cells 34 which have not adhered to the surface of the cell culture substrate 41 can be removed from the cell culture instrument 30 by being washed with a culture medium, a buffer solution, or the like. In this way, it is possible to selectively arrange the cells 34 in the area A1.

(Cell Sorting Method)

Figure 7A:
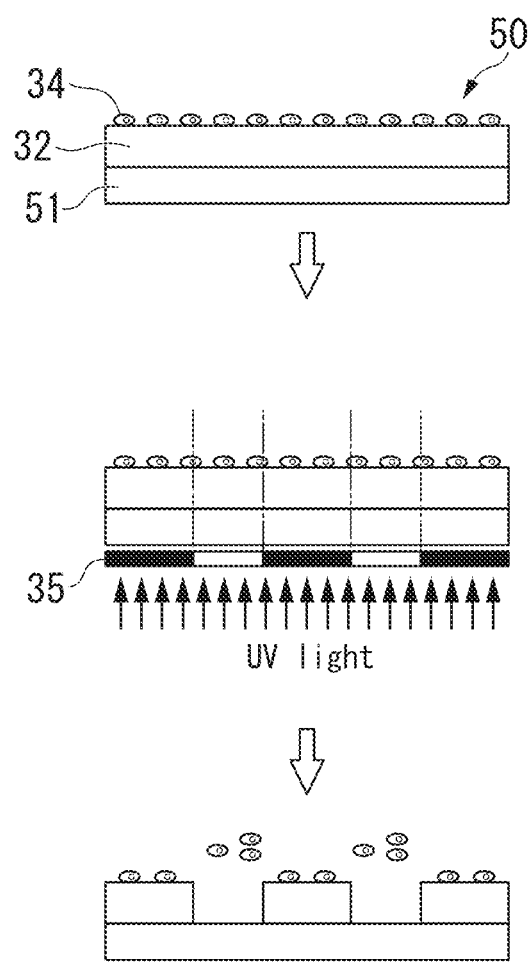
FIG. 7A is a schematic view showing an example of a cell sorting method of the present invention.

Next, a first exemplary cell sorting method will be specifically described with reference to FIG. 7A. FIG. 7A is a schematic view of a cell culture instrument 50.

The photodegradable gel layer 32 is formed on the surface of a cell culture substrate 51.

The material of the cell culture substrate 51 is not particularly limited, and the materials described above can be used. The photodegradable gel layer 32 preferably has high cell adhesiveness. The polymer compound cross-linked with the photodegradable cross-linking agent of the present invention contained in the photodegradable gel layer 32 is preferably the cell-adhesive protein described above.

The photodegradable gel layer 32 may be a mixed material in which the photodegradable gel is mixed with the cell-adhesive material.

When the photodegradable gel layer 32 does not contain the cell-adhesive material, a coating layer containing the photodegradable gel and the cell-adhesive protein may be formed on the photodegradable gel layer 32.

When being seeded into the cell culture instrument 50, the cells 34 adhere onto the surface of the photodegradable gel layer 32.

The area A1 as a portion of the photodegradable gel layer 32 of the cell culture instrument 50 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 32 is three-dimensionally processed. Furthermore, the cells 34 which have adhered to the photodegradable gel of the area A1 are exfoliated from the cell culture substrate 51.

By being washed with a culture medium, a buffer solution, or the like, the exfoliated cells 34 can be selectively removed from the cell culture instrument 50.

In this way, the cells can be sorted into the cells 34 of the area A1 and other cells 34.

Figure 7B:
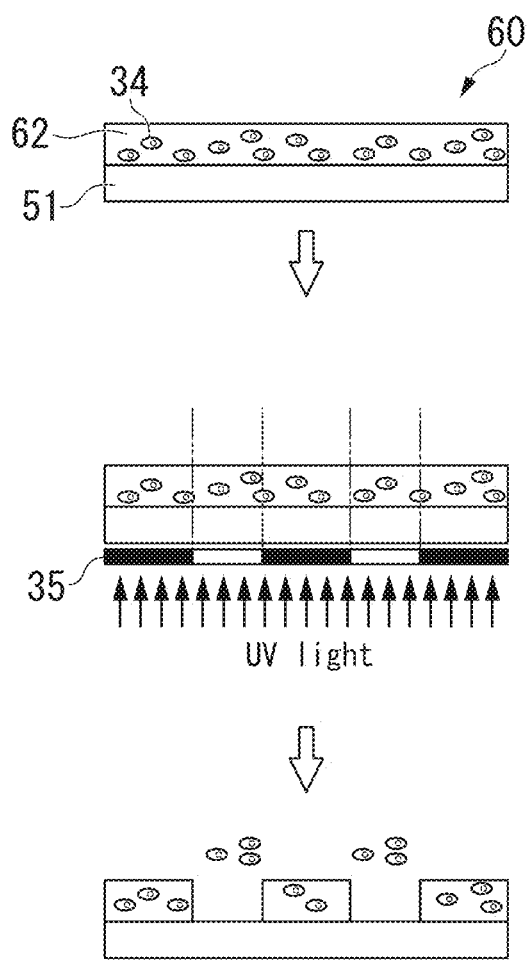
FIG. 7B is a schematic view showing another example of the cell sorting method of the present invention.

Hereinafter, a second exemplary cell sorting method will be specifically described with reference to FIG. 7B. FIG. 7B is a schematic view of a cell culture instrument 60.

A photodegradable gel layer 62 in which the cells 34 are embedded is formed on the surface of the cell culture substrate 51.

The material of the cell culture substrate 51 is not particularly limited, and the material described above can be used. The polymer compound cross-linked with the photodegradable cross-linking agent of the present invention contained in the photodegradable gel layer 62 is not particularly limited as long as it is a polymer compound having a total of two or more amino groups or hydroxyl groups in a molecule. The polymer compound is preferably at least one kind of compound selected from the group consisting of polyethylene glycol, polyvinyl alcohol, basic polysaccharide, a protein, and a derivative of any of these, and more preferably a derivative of branched polyethylene glycol or gelatin.

The area A1 as a portion of the photodegradable gel layer 62 of the cell culture instrument 60 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 62 is three-dimensionally processed. Furthermore, the cells 34 embedded in the photodegradable gel of the area A1 are exfoliated from the cell culture substrate 51.

By being washed with a culture medium, a buffer solution, or the like, the exfoliated cells 34 can be selectively removed from the cell culture instrument 60.

In this way, the cells can be sorted into the cells 34 of the area A1 and other cells 34.

According to the cell arrangement method and the cell sorting method described above, because only the area A1 of the cell culture instrument 11 is irradiated with light, the negative influence exerted on the cells 34 by the light irradiation can be suppressed as much as possible. Consequently, it is possible to prevent the damage of the extracellular matrix or the membrane protein of the cells 34 and to maintain the organ-specific functions thereof. Therefore, the cell arrangement method and the cell sorting method of the present invention are useful in the fields of cell engineering, regenerative medical techniques, bio-industries tissue-engineering, and the like.

Furthermore, because the cells 34 are sorted by irradiating only the area A1 with light, target cells can be sorted out with high accuracy.

The photodegradable gel of the present invention is a material preferable as a cell carrier which can construct a complicated three-dimensional microstructure. Therefore, according to the cell arrangement method and the cell sorting method of the present invention, it is possible to three-dimensionally arrange and sort cells with high accuracy.

<<Tissue Forming Method>>

The tissue of the present invention refers to a three-dimensional assembly of cells, and may contain the photodegradable gel of the present invention between the cells. It is preferable that the cells are cultured for a certain period of time, to grow, form an intended tissue, and be differentiated into an intended state, by using the photodegradable gel of the present invention.

The tissue forming method of the present invention includes a step of forming a photodegradable gel. The thickness of the photodegradable gel is preferably equal to or greater than 10 μm which makes it possible for the cells embedded in the gel to be arranged by at least two or more cells in the Z-axis direction and makes it possible to form a three-dimensional tissue. More specifically, the thickness of the photodegradable gel is preferably 20 μm to 1,000 μm, and more preferably 50 μm to 300 μm.

In the tissue forming method of the present invention, after the photodegradable gel is formed, the photodegradable gel is irradiated with light. In this way, the photodegradable gel can be partially or entirely degraded, and at least a portion of the photodegradable gel can be removed from the tissue.

Hereinafter, a case in which the cell culture instrument of the present invention is used for the tissue forming method will be described. However, the tissue forming method of the present invention only needs to use the photodegradable gel of the present invention, and may be performed without using the cell culture instrument of the present invention.

Next, a tissue forming method including the following steps will be described.

(I) A step of forming the photodegradable gel of the present invention (II) A step of specifying the shape of the photodegradable gel by light irradiation (III) A step of seeding cells into the photodegradable gel (IV) A step of culturing the cells The order of the steps (I) to (IV) may be appropriately switched. Alternatively, any of the steps may be performed two or more times.

Figure 8A:
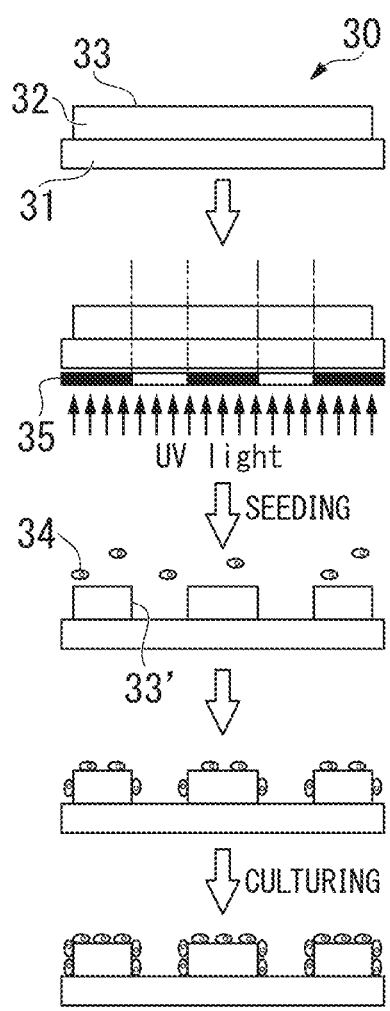
FIG. 8A is a schematic view showing a first example of a tissue forming method of the present invention.

Hereinafter, a first exemplary tissue forming method will be specifically described with reference to FIG. 8A. FIG. 8A is a schematic view of the cell culture instrument 30.

The cell culture substrate 31 and the photodegradable gel layer 32 can use the same constitution as in the first exemplary cell arrangement method.

The area A1 as a portion of the photodegradable gel layer 32 of the cell culture instrument 30 is irradiated with light through the photomask 35, thereby degrading the photodegradable gel layer 32 of the area A1. The photodegradable gel of the area A1 is solubilized and removed from the surface of the cell culture substrate 31 by washing. In this way, the photodegradable gel layer 32 is three-dimensionally processed and shaped according to the pattern of the photomask.

When being seeded into the cell culture instrument 30, the cells 34 adhere only to the surface 33 of the photodegradable gel layer 32 and the surface 33' of the photodegradable gel layer that is newly formed by the light irradiation.

The cells 34 which have not adhered to the surfaces 33 and 33' of the photodegradable gel layer 32 can be removed from the cell culture instrument 30 by being washed with a culture medium, a buffer solution, or the like. In this way, it is possible to selectively arrange the cells 34 on the three-dimensionally processed photodegradable gel layer 32.

Thereafter, by culturing, the cells 34 can grow by using the processed photodegradable gel layer 32 as a scaffold, and a tissue can be three-dimensionally formed on the cell culture instrument 30.

Figure 8B:
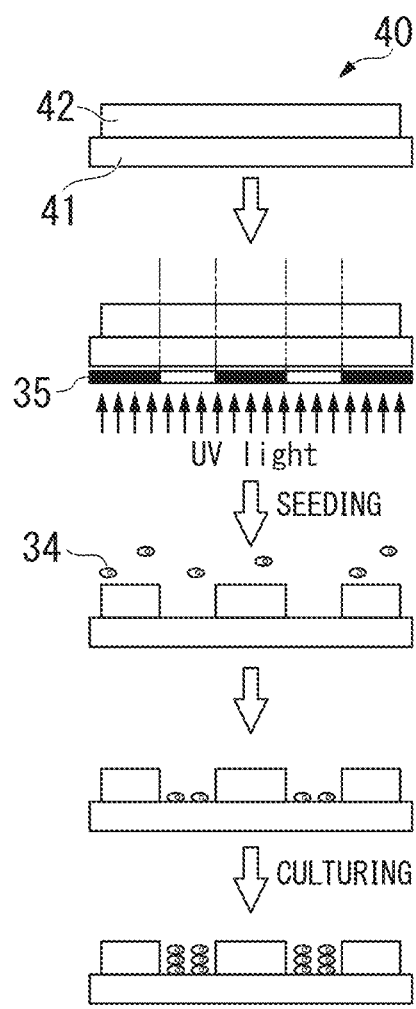
FIG. 8B is a schematic view showing a second example of the tissue forming method of the present invention.

Hereinafter, a second exemplary tissue forming method will be specifically described with reference to FIG. 8B. FIG. 8B is a schematic view of the cell culture instrument 40.

The photodegradable gel layer 42 is formed on the surface of the cell culture substrate 41.

The cell culture substrate 41 and the photodegradable gel layer 42 can use the same constitution as in the second exemplary cell arrangement method.

As the cells, those growing without depending on cell-matrix adhesion are preferable, and examples thereof include tumor cells, hematopoietic cells, various stem cells, and the like.

The area A1 as a portion of the photodegradable gel layer 42 of the cell culture instrument 40 is irradiated with light through the photomask 35, thereby degrading the photodegradable gel layer 42 of the area A1. The photodegradable gel of the area A1 is solubilized and removed from the surface of the cell culture substrate 41 by washing. In this way, the photodegradable gel layer 42 is three-dimensionally processed.

When being seeded into the cell culture instrument 40, the cells 34 adhere only to the surface of the cell culture substrate 41 of the area A1 from which the photodegradable gel layer 42 has been removed.

The cells 34 which have not adhered to the surface of the cell culture substrate 41 can be removed from the cell culture instrument 30 by being washed with a culture medium, a buffer solution, or the like. In this way, it is possible to selectively arrange the cells 34 in the area A1.

Thereafter, by culturing, the cells 34 can grow in a specified shape in the processed photodegradable gel layer 42, and a tissue can be three-dimensionally formed on the cell culture instrument 40.

Figure 8C:
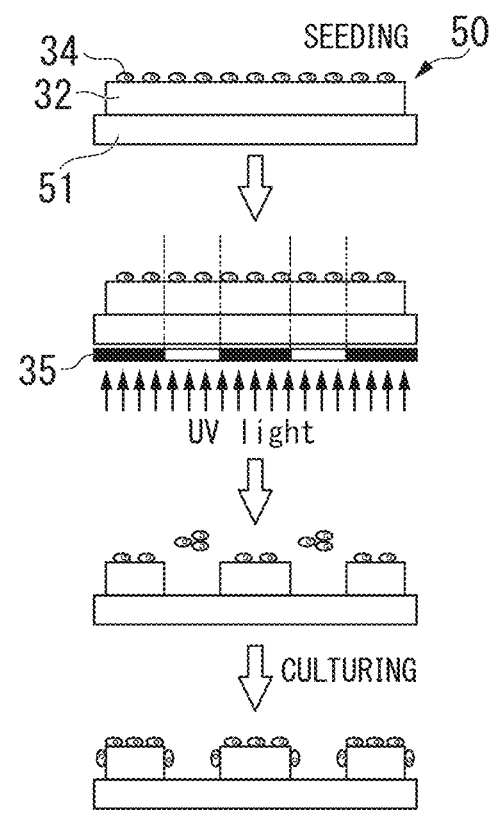
FIG. 8C is a schematic view showing a third example of the tissue forming method of the present invention.

Hereinafter, a third exemplary tissue forming method will be specifically described with reference to FIG. 8C. FIG. 8C is a schematic view of the cell culture instrument 50.

First, the photodegradable gel layer 32 is formed on the surface of the cell culture substrate 51.

The cell culture substrate 51 and the photodegradable gel layer 32 can use the same constitution as in the first exemplary cell sorting method. In this case, it is inappropriate to form a coating layer containing a photodegradable gel and a cell-adhesive protein on the photodegradable gel layer 32.

When being seeded into the cell culture instrument 50, the cells 34 adhere to the surface of the photodegradable gel layer 32.

The area A1 as a portion of the photodegradable gel layer 32 of the cell culture instrument 50 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 32 is three-dimensionally processed. Furthermore, the cells 34 having adhered to the photodegradable gel of the area A1 are exfoliated from the surface of the cell culture substrate 51.

By being washed with a culture medium, a buffer solution, or the like, the exfoliated cells 34 can be selectively removed from the cell culture instrument 50.

In this way, the cells are sorted into the cells 34 of the area A1 and other cells 34.

Thereafter, by culturing, the cells 34 can grow by using the processed photodegradable gel layer 32 as a scaffold, and a tissue can be three-dimensionally formed on the cell culture instrument 50.

Figure 8D:
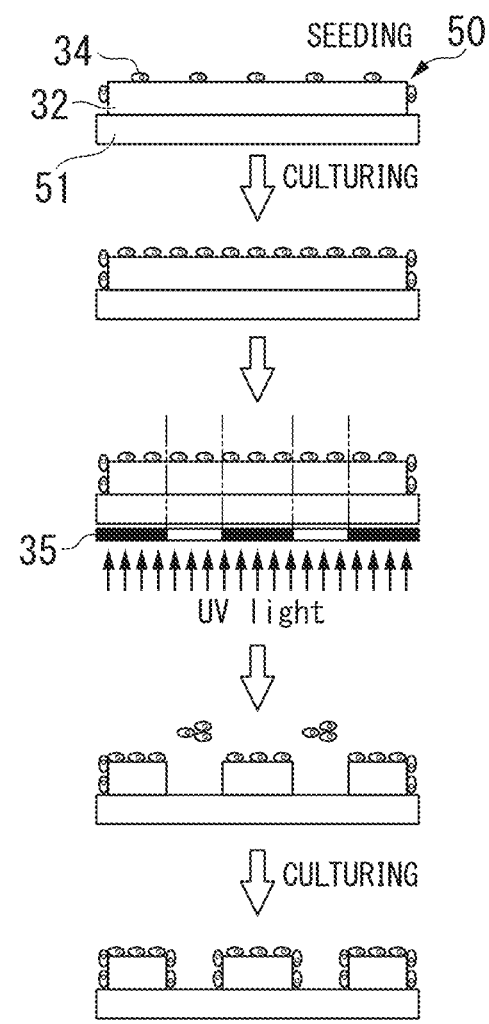
FIG. 8D is a schematic view showing a fourth example of the tissue forming method of the present invention.

Hereinafter, a fourth exemplary tissue forming method will be specifically described with reference to FIG. 8D. FIG. 8D is a schematic view of the cell culture instrument 50.

First, the photodegradable gel layer 32 is formed on the surface of the cell culture substrate 51.

The cell culture substrate 51 and the photodegradable gel layer 32 can use the same constitution as in the first exemplary cell sorting method. In this case, it is inappropriate to form a coating layer containing a photodegradable gel and a cell-adhesive protein on the photodegradable gel layer 32.

When being seeded into the cell culture instrument 50, the cells 34 adhere to the surface of the photodegradable gel layer 32.

Thereafter, by culturing the cells 34, a cell layer can be formed on the cell culture instrument 50.

In addition, the area A1 as a portion of the photodegradable gel layer 32 of the cell culture instrument 50 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 32 can be three-dimensionally processed. Furthermore, the cells 34 having adhered to the photodegradable gel of the area A1 are exfoliated from the surface of the cell culture substrate 51.

By being washed with a culture medium, a buffer solution, or the like, the exfoliated cells 34 can be selectively removed from the cell culture instrument 50.

In this way, it is possible to selectively remove the cells from the cell layer on the cell culture instrument 50.

By being further cultured on the processed gel, the cells 34 can grow by using the processed photodegradable gel layer 32 as a scaffold, and a tissue can be three-dimensionally formed on the cell culture instrument 50.

Next, a tissue forming method including the following steps will be described.

(I) A step of forming the photodegradable gel in which cells are embedded (II) A step of specifying the shape of the photodegradable gel by light irradiation (III) A step of culturing the cells The order of the steps (I) to (III) can be appropriately switched. Alternatively, any of the steps may be performed two or more times.

The cell culture substrate 51 and the photodegradable gel layer 62 can use the same constitution as in the second exemplary cell sorting method.

Figure 9A:
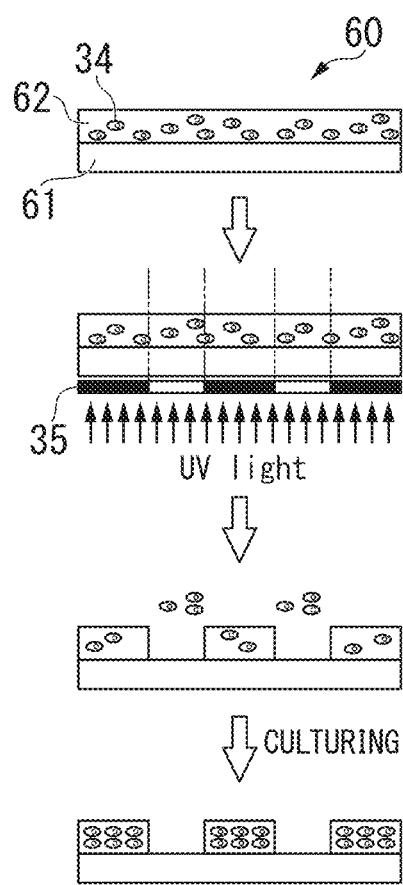
FIG. 9A is a schematic view showing a fifth example of the tissue forming method of the present invention.

Hereinafter, a fifth exemplary tissue forming method will be specifically described with reference to FIG. 9A. FIG. 9A is a schematic view of the cell culture instrument 60.

The photodegradable gel layer 62 in which the cells 34 are embedded is formed on the surface of the cell culture substrate 51.

The area A1 as a portion of the photodegradable gel layer 62 of the cell culture instrument 60 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 62 is three-dimensionally processed. Furthermore, the cells 34 embedded in the photodegradable gel of the area A1 are exfoliated from the surface of the cell culture substrate 51.

By being washed with a culture medium, a buffer solution, or the like, the exfoliated cells 34 can be selectively removed from the cell culture instrument 60.

In this way, the cells are sorted into the cells 34 of the area A1 and other cells 34.

Thereafter, by culturing, the cells 34 can grow in a specified shape within the processed photodegradable gel layer 62, and a tissue can be three-dimensionally formed on the cell culture instrument 60.

Figure 9B:
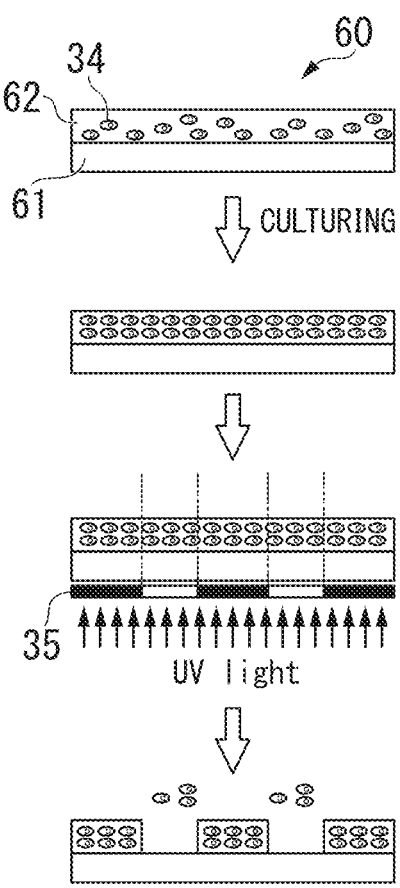
FIG. 9B is a schematic view showing a sixth example of the tissue forming method of the present invention.

Hereinafter, a sixth exemplary tissue forming method will be specifically described with reference to FIG. 9B. FIG. 9B is a schematic view of the cell culture instrument 60.

The photodegradable gel layer 62 in which the cells 34 are embedded is formed on the surface of the cell culture substrate 51.

Thereafter, by culturing the cells 34, a lump of cells can be three-dimensionally formed on the cell culture instrument 60.

The area A1 as a portion of the photodegradable gel layer 62 of the cell culture instrument 60 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 62 is three-dimensionally processed. Furthermore, the cells 34 embedded in the photodegradable gel of the area A1 are exfoliated from the surface of the cell culture substrate 51.

By being washed with a culture medium, a buffer solution, or the like, the exfoliated cells 34 can be selectively removed from the cell culture instrument 60.

In this way, the cells can be sorted into the cells 34 of the area A1 and other cells 34, and cells can be removed from the lump of cells that is three-dimensionally formed on the cell culture instrument 60. Thereafter, by culturing, the cells 34 can grow in a specified shape in the processed photodegradable gel layer 62, and a tissue can be three-dimensionally formed on the cell culture instrument 60.

Hereinafter, a seventh exemplary tissue forming method will be specifically described with reference to FIG. 9C. FIG. 9C is a schematic view of the cell culture instrument 60.

The photodegradable gel layer 62 in which the cells 34 are embedded is formed on the surface of the cell culture substrate 51.

The area A1 as a portion of the photodegradable gel layer 62 of the cell culture instrument 60 is irradiated with light through the photomask 35, thereby degrading the photodegradable gel of the area A1. The photodegradable gel of the area A1 is solubilized and removed from the surface of the cell culture substrate 51 by washing. In this way, the photodegradable gel layer 62 is three-dimensionally processed. Furthermore, the cells 34 embedded in the photodegradable gel of the area A1 are exfoliated from the surface of the cell culture substrate 51.

By being washed with a culture medium, a buffer solution, or the like, the exfoliated cells 34 can be selectively removed from the cell culture instrument 60.

In this way, the cells can be sorted into the cells 34 of the area A1 and other cells 34.

Thereafter, a photodegradable gel layer 72 in which a different type of cells 34' from the cells 34 are embedded may be additionally formed on the cell culture substrate 51 or the photodegradable gel layer 62 exposed to light by the light irradiation.

The photodegradable gel layers 62 and 72 can be processed again by, for example, irradiating an area B1, which is different from the area A1, with light through the photomask 35.

Thereafter, by culturing, the cells 34 and 34' can grow in a specified shape in the processed photodegradable gel layers 62 and 72, and a tissue can be three-dimensionally formed on the cell culture instrument 60.

The photodegradable gel of the present invention is a material preferable as a cell carrier which can construct a complicated three-dimensional microstructure. Therefore, according to the tissue forming method of the present invention, it is possible to form a tissue having a complicated three-dimensional microstructure. Furthermore, a highly reliable cellular assay system closer to the biological environment can be realized.

EXAMPLES

Next, the present invention will be more specifically described by illustrating examples, but the present invention is not limited to the following examples.

Example 1

[Synthesis of Photodegradable Cross-Linking Agent]
The method for synthesizing a photodegradable cross-linking agent (NHS-PD-4arm PEG) is as follows.
4-{4-[1-(9-Fluorenylmethyloxycarbonylamino)ethyl]-2-methoxy-5-nitrophenoxy}butanoic acid (2.7 g) was added to a DMSO solution (130 mL) of 3-(1-piperazino)propyl functionalized silica gel (66 g) washed with N,N-dimethylsulfoxide (DMSO), and the resultant was stirred for tens of minutes to 24 hours under a reflux condition at room temperature. After the resultant was filtered, the substance separated by filtration was washed with DMSO, and then DMSO was distilled away under reduced pressure until the total amount of the resultant became about 130 mL. To the obtained residue, a tetrahydrofuran (THF) solution of SUNBRIGHT PTE-100 HS (manufactured by NOF CORPORATION, 9.6 g) was added, and the resultant was stirred for tens of minutes to 24 hours under a reflux condition at room temperature. After THF was distilled away from the reaction mixture under reduced pressure, the residue was slowly added dropwise to cooled ether. The resultant was left to stand for several hours to 3 days, and then the precipitate was collected by filtration. A small amount of the precipitate was dissolved in THF and then slowly added dropwise to cooled ether. The resultant was left to stand for 1 hour to 24 hours, and then the precipitate was collected by filtration (repeated twice). The precipitate was dried under reduced pressure and then separated and purified by using Sephadex LH-20 (MeOH). To a THF solution of the compound obtained as above, N-hydroxysuccinimide (NHS) and 1-ethyl-3-(3-dimethylaminopropyl)carbodiimide hydrochloride (EDC) were added, and the resultant was stirred for tens of minutes to 24 hours under a condition of reflux at room temperature. From the reaction mixture, THF was distilled away under reduced pressure, and then dichloromethane ($CH_2Cl_2$) was added thereto for dilution. The obtained $CH_2Cl_2$ solution was washed with a 5% aqueous hydrochloric acid solution and saturated saline. Thereafter, the resultant was dried over anhydrous magnesium sulfate and filtered, and then the solvent was distilled away under reduced pressure. The residue dissolved in a small amount of THF was slowly added dropwise to ether, the resultant was left to stand for 1 hour to 24 hours, and then the precipitate was separated by filtration (repeated twice). The precipitate was dried under reduced pressure, thereby obtaining 9.80 g of a photodegradable cross-linking agent as a target compound.

Figure 10:
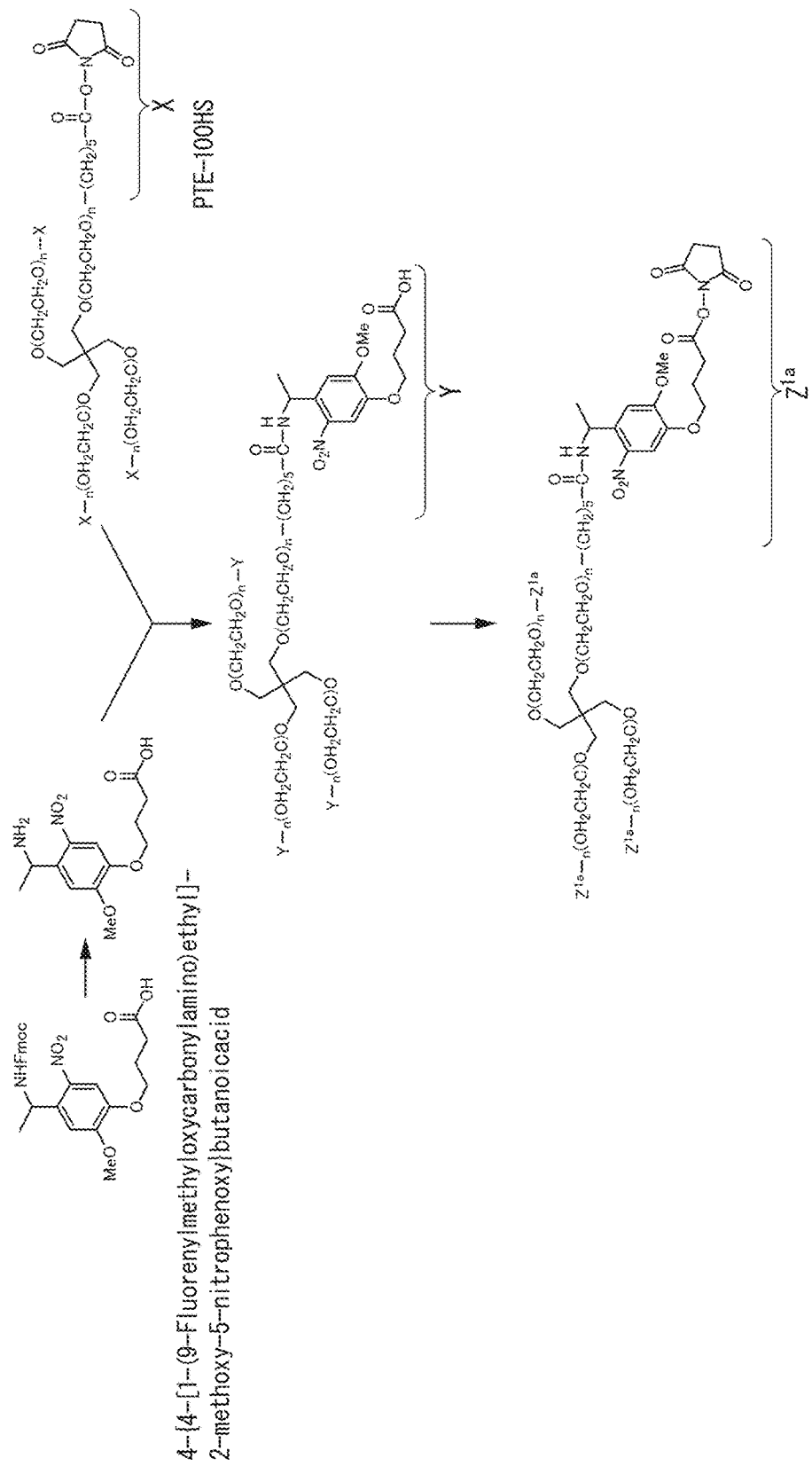
FIG. 10 is a view illustrating an example of the synthesis of the photodegradable cross-linking agent of the present invention.

The process described above and the obtained compound are shown in FIG. 10.

By NMR analysis performed on the obtained target compound, it was confirmed that the obtained compound is an intended compound. The NMR analysis results are shown below.

$^1$H-NMR (400 MHz, $CDCl_3$): 1.35 (m, 2H), 1.53 (d, J=7.09 Hz, 3H), 1.60 (m, 4H), 2.18 (br t, J=7.21 Hz, 2H), 2.28 (tt, J=7.33, 5.98 Hz, 2H), 2.85 (br s, 4H), 2.88 (t, J=7.33 Hz, 2H), 3.41 (s, 2H), 3.43 (t, J=7.21 Hz, 2H), 3.47-3.83 (m, $O(CH_2CH_2O)_n$), 3.94 (s, 3H), 4.15 (t, J=5.98 Hz, 2H), 5.49 (dq, J=7.57, 7.09 Hz, 1H), 6.39 (br d, J=7.57 Hz, 1H), 6.91 (s, 1H), 7.56 (s, 1H)

Example 2

[Manufacturing Photodegradable Gel] (Gelatin Solution)
Gelatin (Type A, 300 Bloom, derived from pig skin) (Gelatin from Porcine skinegel strength 300, Sigma-Aldrich Co, LLC.) (5 w/v %)
Solvent (phosphate buffer solution (DPBS):0.3 Mm HEPES=1:1, pH 7)
In the amount described above, the gelatin and the solvent were stirred and mixed together at a temperature of 37° C., thereby obtaining a gelatin solution.
(Photodegradable Cross-Linking Agent Solution)
Photodegradable cross-linking agent (synthesized in Example 1) 10 Mm (12.1 w/v %)
Solvent (aqueous solution containing 140 mM NaCl and 10 mM phthalic acid)
(Photodegradable Gel Solution)
The gelatin solution and the photodegradable cross-linking agent were mixed together in an equal amount, thereby obtaining a gelatin-based photodegradable gel solution.

Example 3

[Amino-4Arm PEG Solution]
amino-4arm PEG (MW=10,000) (SUNBRIGHT PTE-100PA, manufactured by NOF CORPORATION) 10 mM (12.1 w/v %)
Solvent (phosphate buffer solution (DPBS):0.3 M HEPES=1:1, pH 7)
In the amount described above, PEG was mixed with the solvent, thereby obtaining an amino-4arm PEG solution.
[Photodegradable Cross-Linking Agent Solution]
Photodegradable cross-linking agent (synthesized in Example 1) 10 mM (12.1 w/v %)
Solvent (aqueous solution containing 140 mM NaCl and 10 mM phthalic acid, pH 4)
(Photodegradable Gel Solution)
The amino-4arm PEG solution and the photodegradable cross-linking agent were mixed together in an equal amount, thereby obtaining a polyethylene glycol-based photodegradable gel solution.

Example 4

Amino-coated slide glass (MAS-coated slide glass, manufactured by Matsunami Glass Ind., Ltd.) was coated with the gelatin-based photodegradable gel solution (10 µL to 30 µL) of Example 2. Thereafter, the slide glass was covered with another slide glass, thereby forming a photodegradable gel layer. The thickness of the gel layer was regulated by the slide glass (thickness: 150 µm) or a PET film (thickness: 25 µm). A mask for photolithography was prepared by printing a pattern on a film at a resolution of 300 dpi.

The mask was disposed between an irradiation apparatus and the slide glass. In this way, the gel is photodegraded by being selectively exposed to light. The gel was irradiated with light at an irradiation energy of 7.2 J/cm$^2$ to 9.0 J/cm$^2$ until the gel was degraded in the form of an intended pattern. As a light source, the one having a wavelength of 350 nm to 385 nm and an intensity of 30 mW/cm$^2$ was used. The gel degraded by the light irradiation was washed of in distilled water.

Figure 11:
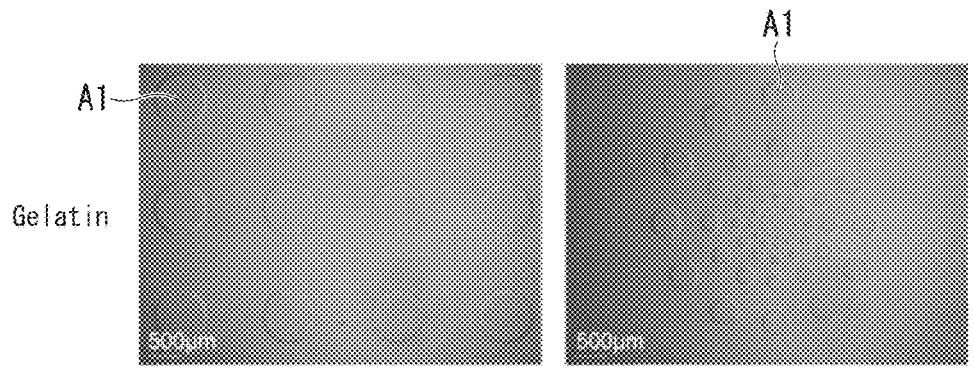
FIG. 11 is a picture of a gelatin-based photodegradable gel of the present invention that is patternwisely degraded by light irradiation.

FIG. 11 is a picture of the gelatin-based photodegradable gel of the present invention that is patternwisely degraded by the light irradiation. It was confirmed that by selectively irradiating the area A1 with light, the gelatin-based photodegradable gel of the present invention can be degraded up to a diameter of 20 μm with high degradability (XY-plane).

Example 5

Amino-coated slide glass (MAS-coated slide glass, manufactured by Matsunami Glass Ind., Ltd.) was coated with the polyethylene glycol-based photodegradable gel solution (10 μL to 30 μL) of Example 3. Thereafter, the slide glass was covered with another slide glass, thereby forming a photodegradable gel layer. The thickness of the gel layer was regulated by using the slide glass (thickness: 150 μm) or a PET film (thickness: 25 μm).

In the same manner as in Example 4, a mask was prepared, and the gel was photodegraded.

Figure 12:
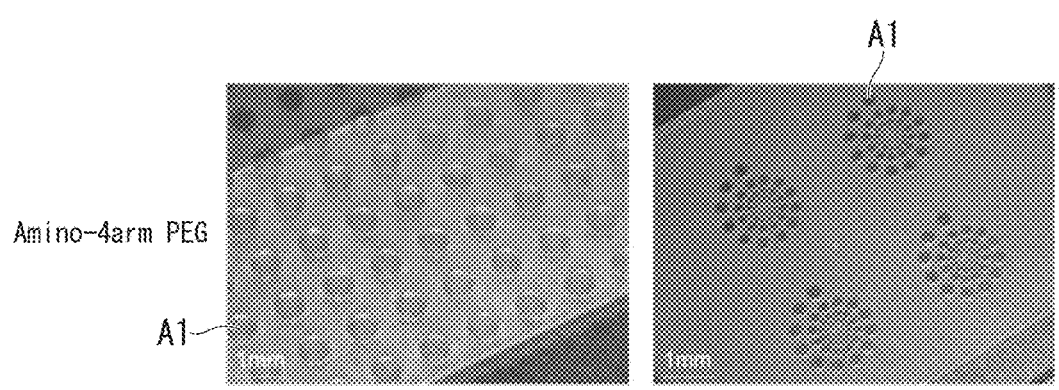
FIG. 12 is a picture of a polyethylene glycol-based photodegradable gel of the present invention that is patternwisely degraded by light irradiation.

FIG. 12 is a picture of the polyethylene glycol-based photodegradable gel of the present invention that is patternwisely degraded by the light irradiation. It was confirmed that by irradiating the area A1 with light, the polyethylene glycol-based photodegradable gel of the present invention can be degraded up to a diameter of 20 μm with high degradability (XY-plane).

Figure 13A:
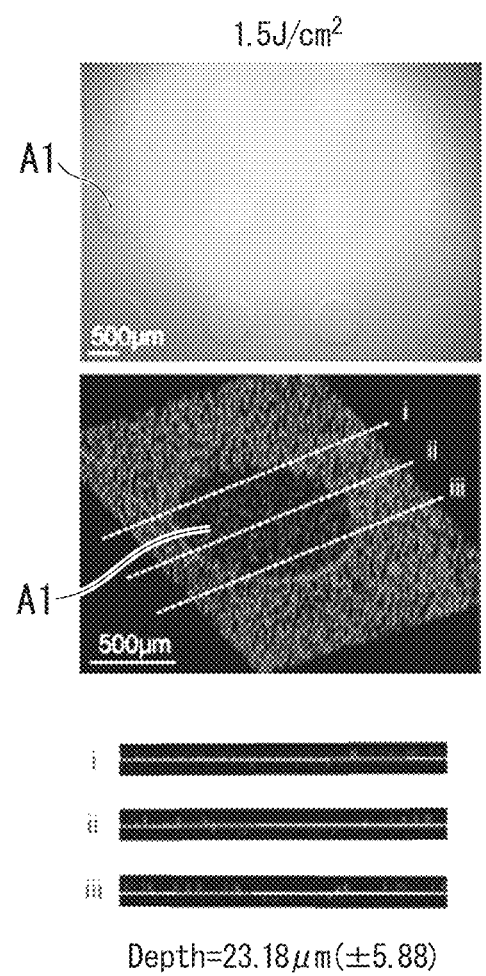
FIG. 13A is a view showing the results obtained by measuring a degradation depth of the photodegradable gel of the present invention in the thickness direction (irradiation energy: 1.5 J/cm$^2$).
Figure 13B:
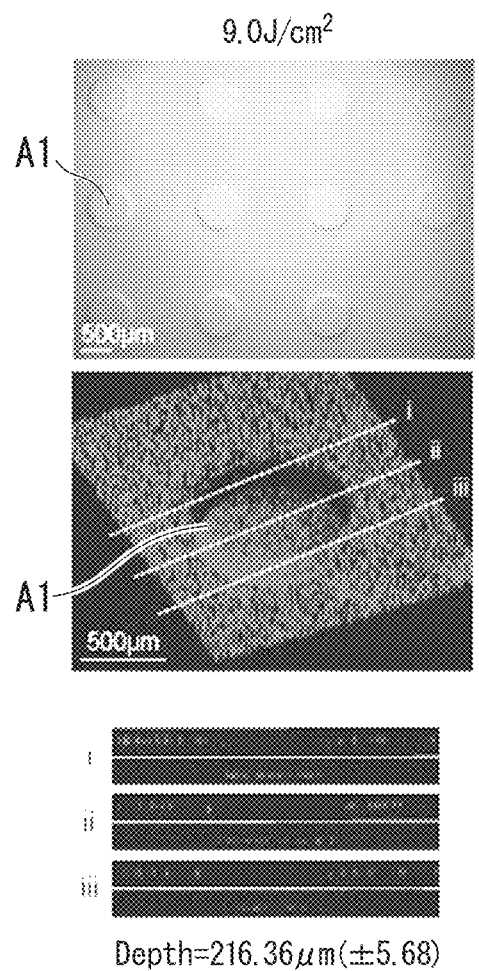
FIG. 13B is a view showing the results obtained by measuring a degradation depth of the photodegradable gel of the present invention in the thickness direction (irradiation energy: 9.0 J/cm$^2$).

The degradability of the photodegradable gel in the Z-axis was also tested. FIG. 13A is an image showing the state of a gel degraded by light by means of irradiating the area A1 with light at an irradiation energy of 1.5 J/cm$^2$. FIG. 13B is an image showing the state of a gel degraded by light by means of irradiating the area A1 with light at an irradiation energy of 9.0 J/cm$^2$. The results obtained by observing the gel surface by using an optical microscope are shown in the upper panels of FIGS. 13A and 13B. Fluorescent beads were localized within the patternwisely degraded gel surface, and by using a confocal laser microscope, the degradation shape and degradation depth of the gel were measured. The image data obtained by the confocal laser microscope are shown in the middle and lower panels of FIG. 13A and in the middle and lower panels of FIG. 13B. The plan views taken along the Z-axis in the position of the broken lines (i), (ii), and (iii) in the middle panels of FIGS. 13A and 13B correspond to (i), (ii), and (iii) of the lower panels of FIGS. 13A and 13B respectively.

Figure 13C:
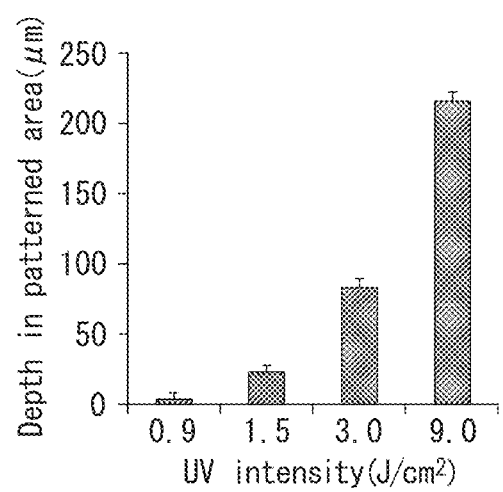
FIG. 13C is a view showing the results obtained by measuring the average depth of a gel layer of the photodegradable gel of the present invention after photodegradation.

FIG. 13C shows the measurement results (n=4) of the average depth of the gel layer that were obtained after the gel layer was photodegraded by irradiating the area A1 with light at an irradiation energy of 0.9 J/cm$^2$ 1.5 J/cm$^2$, 3.0 J/cm$^2$, and 9.0 J/cm$^2$. In the polyethylene glycol-based photodegradable gel of the present invention, the stronger the irradiation energy, the greater the degradation depth in the Z-axis direction within the area A1. At an irradiation energy of 9.0 J/cm$^2$, the gel layer was degraded to a depth of 216 μm inside the gel.

From these results, it was confirmed that the photodegradable gels of Examples 4 and 5 of the present invention can be microfabricated by the light irradiation in any of the directions of X, Y, and Z axes.

Example 6

[Embedding Cells into Photodegradable Gel]

The cells 34 (mouse fibroblasts: NIH-3T3) were added to the amino-4arm PEG solution of Example 3, and the photodegradable cross-linking agent solution was added thereto in the same manner as in Example 3, thereby obtaining a photodegradable gel solution containing the cells 34. Thereafter, the gel layer 62 in which the cells 34 were embedded was formed on slide glass, and the gel was patternwisely degraded by irradiating the area A1 with light. The formation of the gel layer and the patternwise degradation of the gel were performed in the same manner as in Example 4.

The gel layer 62, in which the cells 34 were embedded and which had been irradiated with light, was stained by using a LIVE/DEAD assay kit (using 0.5 μL ethidium homodimer-1 and 2.0 μL of calcein AM (manufactured by Molecular Probes)) so as to check whether the cells 34 were dead or alive.

By the staining, living cells give off a green fluorescence, and dead cells give off a red fluorescence.

Figure 14A:
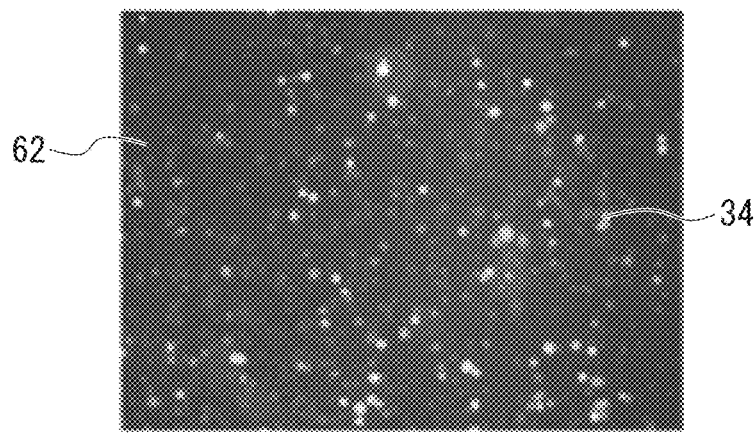
FIG. 14A shows the form of cells embedded in the photodegradable gel (before light irradiation).
Figure 14B:
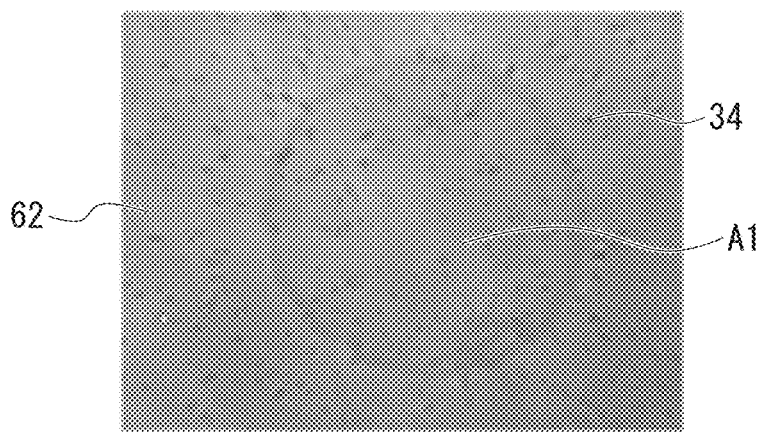
FIG. 14B shows the form of cells embedded in the photodegradable gel (after light irradiation; observed in a bright field).
Figure 14C:
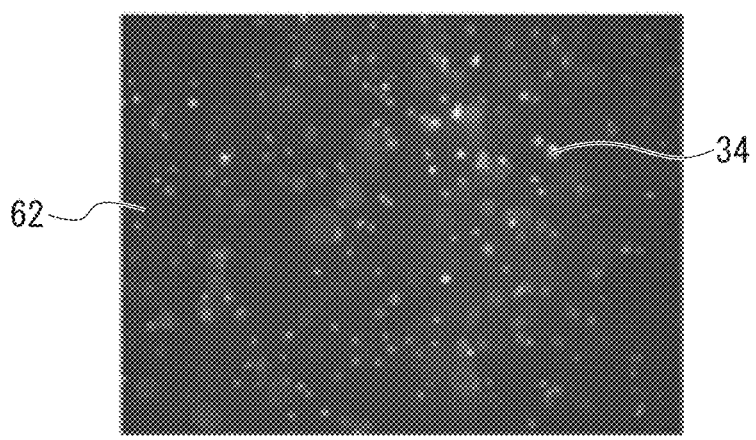
FIG. 14C shows the form of cells embedded in the photodegradable gel (after light irradiation; fluorescence observation).

FIGS. 14A to 14C show the form of the stained cells. FIG. 14A is a fluorescence observation image of the gel layer 62 having not yet been irradiated with light. FIG. 14B is an image obtained by observing the gel layer 62, which is patterned after being irradiated with light, in a bright field. FIG. 14C is a fluorescence observation image of FIG. 14B. In the gel having been irradiated with light, 70% or more of the cells 34 embedded in the gel layer gave off a green fluorescence. Therefore, it was revealed that even after the cells 34 are embedded into the photodegradable gel of the present invention, and the gel is patterned by the light irradiation, the cells 34 can survive in an excellent state.

From the above results, it was understood that the photodegradable gel of the present invention using the photodegradable cross-linking agent of the present invention can form a three-dimensional microstructure while keeping cells alive in the gel. Accordingly, the photodegradable gel of the present invention using the photodegradable cross-linking agent of the present invention is an extremely useful tissue engineering material which is suited for forming a complicated three-dimensional microstructure.

Example 7

[Preparation of Photodegradable Gel]

10 mM amino-4arm PEG (Mw=9617, manufactured by NOF CORPORATION) or 5% (w/w) gelatin (Type A, 300 Bloom, derived from pig skin) was mixed with a phosphate buffer solution (PBS, manufactured by Invitrogen) and a 0.3 M HEPES buffer solution (manufactured by Wako Pure Chemical Industries, Ltd.) (pH=7.0) in an equal amount, and the prepared solution mixture was used as a base polymer solution. Furthermore, a synthesized NHS-PC-4arm PEG cross-linking agent (10 mM, 12.1% w/w) was mixed with a 10 mM phthalate buffer solution (pH 4.0, manufactured by Wako Pure Chemical Industries, Ltd.), thereby preparing a cross-linking agent solution. In addition, the prepared cross-linking agent solution was adjusted to become 140 mM NaCl (manufactured by Wako Pure Chemical Industries, Ltd.). Herein, the gelatin solution was prepared at a temperature of 37° C., and other solutions were prepared at room temperature.

The prepared base polymer solution and the cross-linking agent solution were mixed together in an equal amount. Amino-coated slide glass (MAS coating, manufactured by Matsunami Glass Ind., Ltd.) was coated with the solution mixture of the photodegradable gel solution and the cross-linking agent in a liquid amount of 10 μL to 30 μL, and then the slide glass was covered with another slide glass, thereby forming a photodegradable gel layer. At this time, the thickness of the gel layer was regulated by using a polyethylene terephthalate (PET) film (thickness: 25 μm) or the cover glass (thickness: 150 μm).

Example 8

[Cell Culturing]

Next, in order to evaluate the behavior of the cells on the photodegradable gel prepared in Example 7, human umbilical vein endothelial cells (HUVEC) were seeded onto the synthesized gel substrate. In the evaluation, the photodegradable gel prepared by using amino-4arm PEG or gelatin as a base polymer was used. Furthermore, HUVEC were cultured in an environment of 5% $CO_2$ and a temperature of 37° C., by using HuMedia EG-2 culture solution (manufactured by KURABO INDUSTRIES LTD.) (containing 2% (v/v) fetal bovine serum, 10 ng/mL of a human epidermal growth factor, 1.34 μg/L of hydrocortisone hemisuccinate, 50 μg/mL of gentamicin, 50 ng/mL of amphotericin B, 5 ng/mL of a human basic fibroblast growth factor, and 10 μg/mL of heparin). The cultured cells were exposed for 5 minutes to a DPBS solution containing 0.1% trypsin, and the cells were recovered. Then, by using HuMedia EG-2 culture solution, a cell suspension having a final cell concentration of $1.0 \times 10^7$ cells/mL was prepared.

The HUVEC were seeded onto the photodegradable gel prepared by using amino-4arm PEG or gelatin. By using 35 μL of the cell suspension, the cells were seeded onto the photodegradable gel, spread over the entire surface of the gel, and then left to stand in the culture instrument. After 1 hour elapsed from the start of culturing, the cells which had not adhered to the surface of the photodegradable gel and the excess culture solution were removed by being aspirated into a pipette, and 3 mL of the culture solution was added to a 35 $mm^2$ culture plate and left to stand again in the culture instrument.

On day 1 and day 3 after the start of culturing, the images of the cells were observed under an inverted microscope. Furthermore, in order to determine whether the cells were dead or alive on day 3 after culturing, the cells were stained by using a LIVE/DEAD assay kit (0.5 μL of ethidium homodimer 1, 2.0 μL of calcein AM (manufactured by Molecular probes)). The cultured cells were stained with the cell staining solution for 10 minutes and washed with DPBS. Thereafter, a bright field image and a fluorescence image of the cells were observed under an inverted microscope.

In addition, in order to evaluate the phototoxicity at the time of the light irradiation and to evaluate the toxicity of the degradation product of the synthesized gel, whether the cells were dead or alive was determined in the same manner as described above by means of the aforementioned technique. On a photodegradable gel synthesized from a photodegradable gel solution using 2.5% (w/v) of gelatin as a base and a cross-linking agent solution containing 1.0% (w/v) of NHS-PC-4arm PEG; HUVEC were cultured for 3 days. Subsequently, the gel was patternwisely irradiated with light (365 nm, 125 mW/$cm^2$, 8 seconds to 24 seconds), and the cells were cultured 3 more hours at a temperature of 37° C., thereby performing a test in which the cells were exposed to the degradation product of the gel. The sample was irradiated with light by using a PC-controlled micro-projection system (DESM-01, manufactured by Engineering System Co.) (see NPL 8).

(Result)

Figure 15:
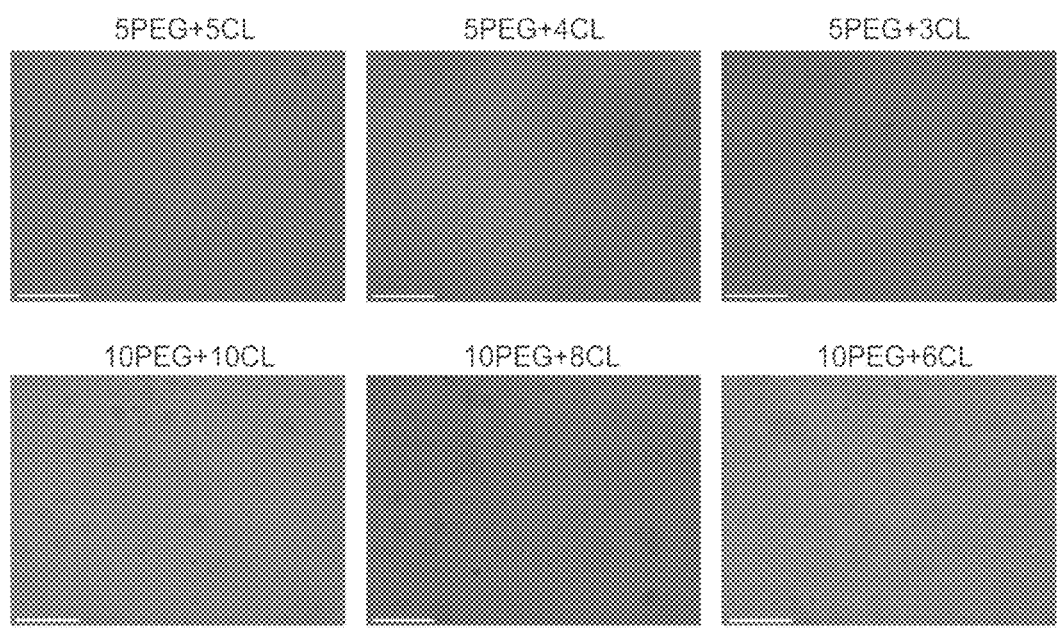
FIG. 15 is a view showing the results obtained by culturing HUVEC for a day on photodegradable gels prepared using components at different concentrations.

In the present example, in order to evaluate the behavior of cells on the photodegradable gel, HUVEC were cultured as model cells. As a result, HUVEC substantially did not adhere onto the surface of the photodegradable gel prepared by using amino-4arm PEG (FIG. 15). Presumably, this is because PEG is a non-cell-adhesive substrate (see NPL 9). In contrast, it was revealed that all of HUVEC adhere onto the surface of gel prepared by using gelatin (FIGS. 16A and 16B).

Figure 16A:
FIG. 16A is a view showing the results obtained by observing the state of HUVEC adhering onto the photodegradable gel by using phase contrast images (culture period: 1 day).
Figure 16B:
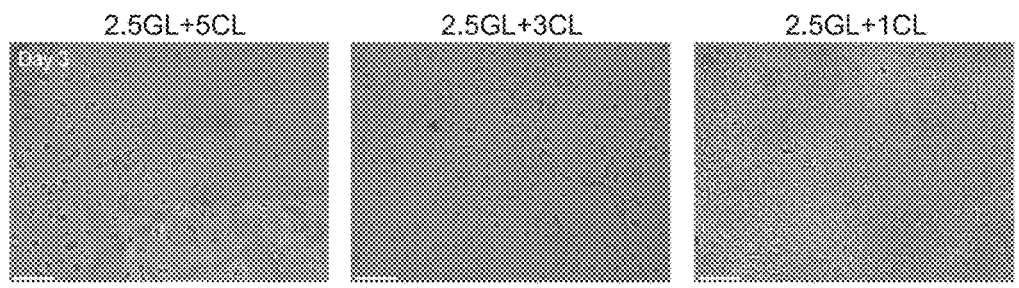
FIG. 16B is a view showing the results obtained by observing the state of HUVEC adhering onto the photodegradable gel by using phase contrast images (culture period: 3 days).
Figure 16C:
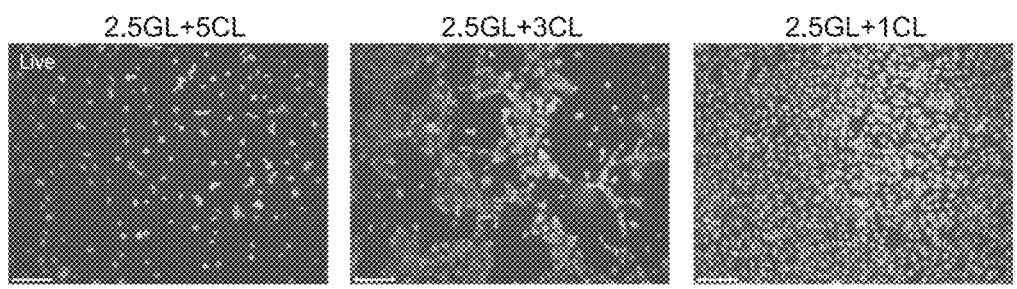
FIG. 16C is a view showing the living HUVEC after 3 days of culturing.
Figure 16D:
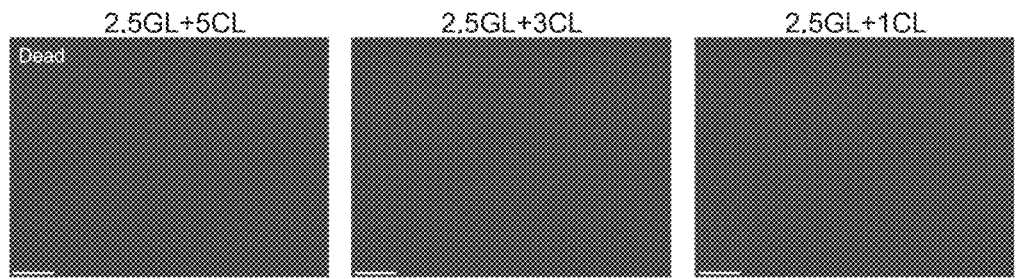
FIG. 16D is a view showing dead HUVEC after 3 days of culturing.

As shown in the right and central panels of FIGS. 16A and 16B, on the gelatin-based photodegradable gel prepared by using the 2.5% (w/v) gelatin solution and the 1.0% (w/v) or 3.0% (w/v) cross-linking agent, marked cell growth was confirmed on day 3 after the start of culturing. This shows that there is a big difference in the cell growth between the aforementioned gel and a gel using the cross-linking agent at a concentration of 5.0% (w/v). The result of the present study implies that the behavior of cells (adhesion of cells onto a substrate, cell elongation on a substrate, and cell growth on a substrate) on a synthesized photodegradable gel is likely to vary with the concentration of the photodegradable cross-linking agent.

Figure 17A:
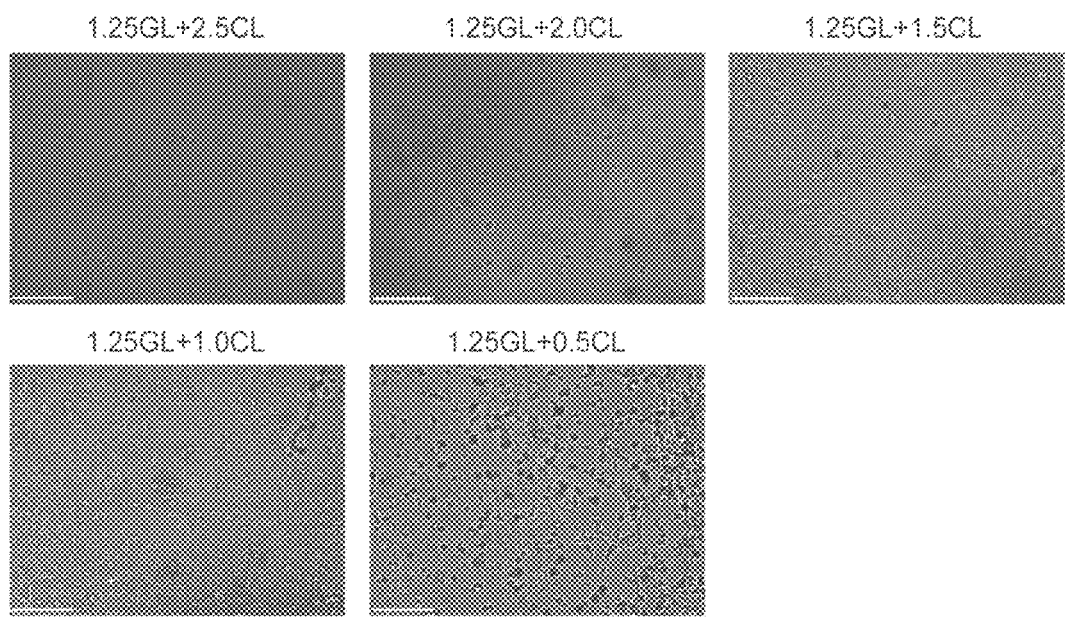
FIG. 17A is a view showing phase contrast images of HUVEC on photodegradable gels prepared using gelatin and cross-linking agents at different concentrations. The bar in the view is 400 μm (culture period: 1 day).
Figure 17B:
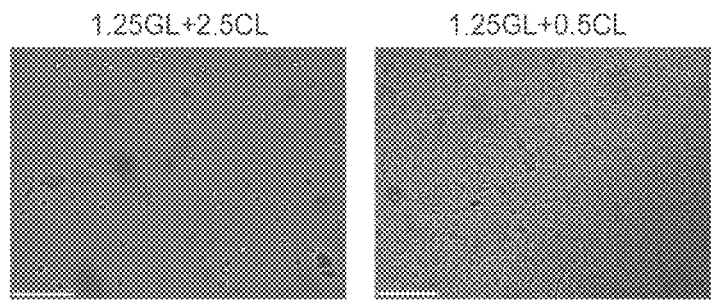
FIG. 17B is a view showing phase contrast images of HUVEC on photodegradable gels prepared using gelatin and cross-linking agents at different concentrations. The bar in the view is 400 μm (culture period: 3 days).

By using the same technique as described above, the cell growth on a photodegradable gel prepared by using a 1.25% (w/v) gelatin solution and a 0.5% (w/v) to 2.5% (w/v) cross-linking agent was studied. As a result, as shown in FIG. 17B, the same trend as in the case of using the 2.5% (w/v) gelatin solution was observed. Therefore, it was revealed that the cell growth is not dependent on the gelatin concentration. Based on the result of the present study, it is considered that the extent of cell adhesion on the photodegradable gel synthesized from a gelatin solution changes depending only on the concentration of the cross-linking agent. That is, it is considered that because the unreacted amino residue on the gelatin substrate remains uninfluenced, the unreacted amino residue is important for the cell adhesion and the cell growth.

Example 9

[Patterning of HUVEC]

In order to test the patterning of HUVEC on a photodegradable gel prepared by using a 2.5% (w/v) gelatin solution and a 1.0% (w/v) cross-linking agent, HUVEC cultured on the same photodegradable gel as in Example 8 was irradiated with light (1.0 J/$cm^2$ to 3.0 J/$cm^2$) through a photomask. Furthermore, in order to evaluate the phototoxicity at the time of light irradiation and to evaluate the cytotoxicity of the degradation product of gel, whether the cells were dead or alive was determined by using a LIVE/DEAD assay kit.

(Result)

Figure 18A:
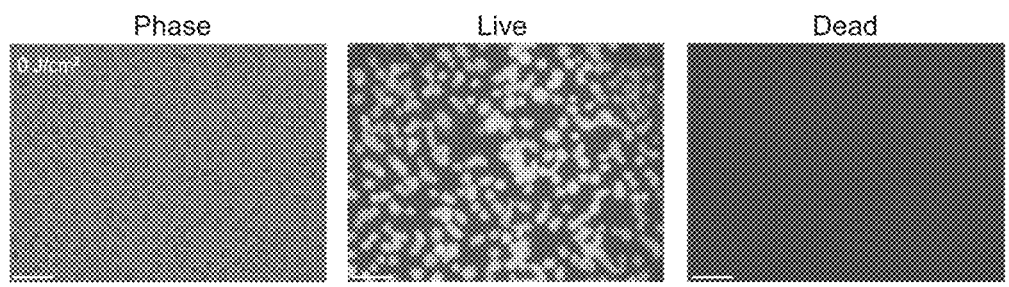
FIG. 18A is a view showing the influence of light irradiation and gel degradation on the viability of cells (light irradiation: 0 J/cm$^2$). The bar in the view is 200 μm.
Figure 18B:
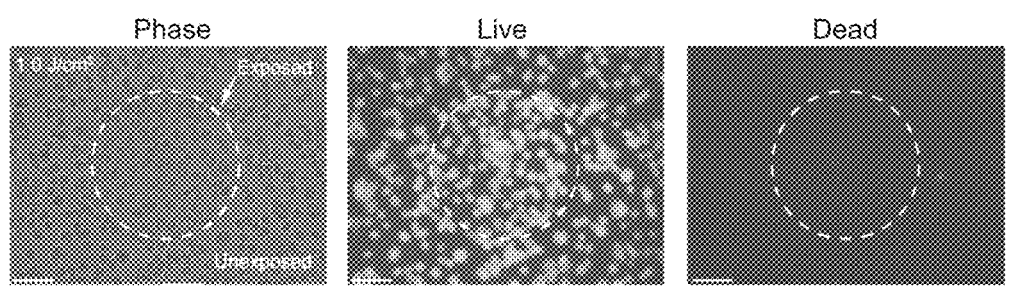
FIG. 18B is a view showing the influence of light irradiation and gel degradation on the viability of cells (light irradiation: 1.0 J/cm$^2$). The bar in the view is 200 μm.
Figure 18C:
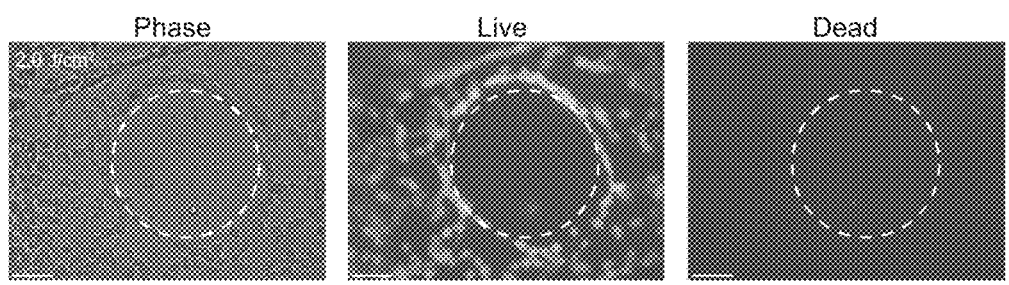
FIG. 18C is a view showing the influence of light irradiation and gel degradation on the viability of cells (light irradiation: 2.0 J/cm$^2$). The bar in the view is 200 μm.
Figure 18D:
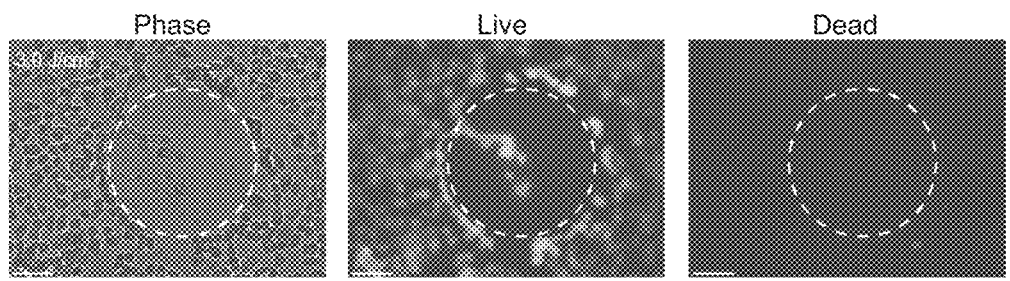
FIG. 18D is a view showing the influence of light irradiation and gel degradation on the viability of cells (light irradiation: 3.0 J/cm$^2$). The bar in the view is 200 μm.

As a result of patterwise degradation of the gel having undergone light irradiation, HUVEC fell into holes of the gel and moved to the periphery from the center (FIGS. 18C and 18D). The pattern of the cells shown in the drawings was formed as a result of the photodegradation of the gel, and this implied that the cells on the gel are likely to be able to be controlled in a micro-order.

In addition, the cells elongated on the gel were irradiated with light, and then whether the cells were dead or alive was determined. As a result, it was confirmed that there is no big difference in the cell survival/death rate between the cells in the region irradiated with light and the cells in the region not irradiated with light (FIGS. 18B to 18D). That is, it was revealed that the survival of cells is not influenced by the light irradiation and the gel degradation.

In the examples described above, it was revealed that a photodegradable gel can be prepared from amino-4arm PEG and gelatin, and a photodegradable hydrogel can be prepared by using a biomolecule having an amino portion as it is. Furthermore, because the photodegradable cross-linking agent described in the present application is considered to be able to react with other naturally occurring polymers (collagen, fibronectin, chitosan, and the like), a possibility of preparing various photodegradable hydrogels is increased.

Each of the constituents, the combination thereof, and the like in each of the embodiments described above is merely an example, and the constituents may be added, omitted, substituted, and modified in other ways within a range that does not depart from the gist of the present invention. Furthermore, the present invention is limited not by the embodiments but only by the scope of claims.

INDUSTRIAL APPLICABILITY

The present invention is useful in the fields of cell engineering, regenerative medical techniques, bio-industries, tissue-engineering, and the like.

REFERENCE SIGNS LIST

1 . . . photodegradable cross-linking agent, 2 . . . main chain, 3 . . . nitrobenzyl group-containing group, 4 . . . active ester group, 5 . . . amide bond portion, 6 . . . polymer compound, 7 . . . polymer compound, 8 . . . amino group, 9 . . . amide bond between cross-linking agent and polymer compound, 10 . . . photodegradable gel, 11•30•40•50•60 . . . cell culture instrument, 31•41•51 . . . cell culture substrate, 32•42•62•72 . . . photodegradable gel layer, 33 . . . surface of photodegradable gel layer, 34 . . . cell, 35 . . . photomask, A1•B1 . . . partial area irradiated with light

The invention claimed is:

1. A photodegradable cross-linking agent comprising:
   a polyethylene glycol main chain which has three or more branched chains; and
   a photodegradable benzyl group which is disposed on the terminus of the polyethylene glycol main chain having the branched chains,
   the benzyl group having an active ester group, which is reactive with an amino group or a hydroxyl group, and one or more nitro groups in a benzene ring of the benzyl group.

2. The photodegradable cross-linking agent according to claim 1,
   wherein the active ester group is a derivative of N-hydroxysuccinimide.

3. The photodegradable cross-linking agent according to claim 1,
   wherein the average repetition number of ethylene glycol in the branched chains is within a range of 20 to 500.

4. The photodegradable cross-linking agent according to claim 1,
   wherein the number of the branched chains is 4 or 8.

5. The photodegradable cross-linking agent according to claim 1,
   wherein the polyethylene glycol main chain has a neopentyl skeleton.

* * * * *